United States Patent [19]

Miya et al.

[11] Patent Number: 4,931,417

[45] Date of Patent: Jun. 5, 1990

[54] TRANSITION-METAL COMPOUND HAVING A BIS-SUBSTITUTED-CYCLOPENTADIENYL LIGAND OF BRIDGED STRUCTURE

[75] Inventors: Shinya Miya; Takashi Yoshimura, both of Ichiharashi; Takaya Mise, Kawagoeshi; Hiroshi Yamazaki, Tokorozawa, all of Japan

[73] Assignees: Chisso Corporation, Osaka; The Institute of Physical & Chemical Research, Saitamaken, both of Japan

[21] Appl. No.: 266,065

[22] Filed: Nov. 2, 1988

[30] Foreign Application Priority Data

Nov. 9, 1987 [JP] Japan .................................. 62-282538
Jun. 20, 1988 [JP] Japan .................................. 63-151665
Jun. 20, 1988 [JP] Japan .................................. 63-151666

[51] Int. Cl.$^5$ .............................................. C08F 4/64
[52] U.S. Cl. ................................. 502/117; 556/11; 556/53; 526/127; 526/150
[58] Field of Search ................. 502/117; 556/11, 53

[56] References Cited

U.S. PATENT DOCUMENTS 4,530,914 7/1985 Ewen et al. .................. 502 117 X
4,752,597 1/1988 Turner ........................... 502/117 X

*Primary Examiner*—Patrick P. Garvin
*Attorney, Agent, or Firm*—Fred Philpitt

[57] ABSTRACT

A novel transition-metal compound having a bis-substituted cyclopentadienyl ligand of bridged structure (I) and a novel mixture of the compound (I) with an aluminoxane (B), each useful as catalyst component(s) for stereoregular olefin polymerization are provided, which compound (I) is expressed by the formula

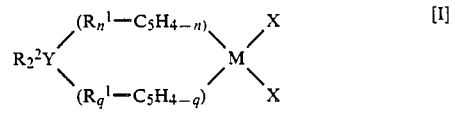

wherein M is Zr or Hf; Y is Si or Ge; $R^1{}_n$-$C_5H_{4-n}$ and $R^1{}_q$-$C_5H_{4-q}$ each represent an unsubstituted or substituted cyclopentadienyl group; n and q each represent an integer of 0 to 4, but cases of n=q=0 and n=q=4 are excluded; $R^1$s may be same or different and each represent H, silyl or hydrocarbon radical; $R^2$s may be same or different and represent H or hydrocarbon radical; and Xs may be same or different and represent H, halogen or hydrocarbon radical; and which aluminoxane is expressed by the formula (II) or the formula (III)

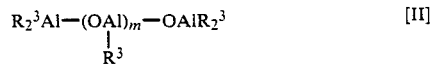

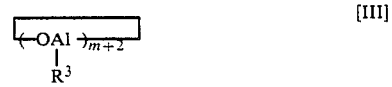

wherein m represents an integer of 4 to 30 and $R^3$ represents a hydrocarbon radical.

2 Claims, 23 Drawing Sheets

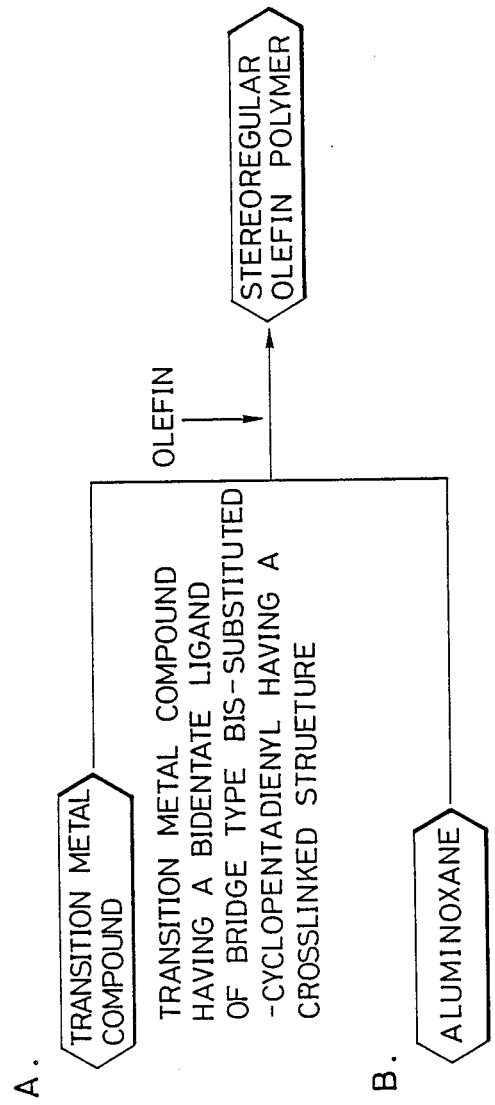

TRANSITION-METAL COMPOUND HAVING A BIS-SUBSTITUTED-CYCLOPENTADIENYL LIGAND OF BRIDGED STRUCTURE

BACKGROUND OF THE INVENTION

1. Field of the Invention

This invention relates to a novel transition-metal compound having a bis-substituted-cyclopentadienyl ligand of bridged structure. The compound of the present invention is useful as a catalyst component for stereo-regular olefin polymerization.

2. Description of the Related Art

As a homogeneous catalyst for olefin polymerization, the so-called Kaminsky catalyst (metallocene compound/aluminoxane) has been well known. The catalyst has a very high polymerization activity, and in the case of propylene polymerization, it has also been known that it is possible to produce both of atactic polypropylene (Makromol. Chem. Rapid Commun. 4,417–421 (1983), Japanese patent application laid-open Nos. Sho 58-19,309/1983, Sho 60-130,604/1985 and Sho 61-211,307/1986) and isotactic polypropylene (Angew. Chem. Int. Ed. Engl. 24,507–508 (1985), J. Am. Chem. Soc. 1984, 106, 6355–6364, Japanese patent application laid-open No. Sho 61-264,010/1986, J. Am. Chem. Soc., 1987, 109, 6544–6545 and Japanese patent application laid-open No. Sho 63-66206/1988), in the presence of the above catalyst.

In the case of metallocene compounds, transition-metal compounds having a bis-unsubstituted-cyclopentadienyl ligand crosslinked with silicon, phosphine, amine or carbon are known (Japanese patent application laid-open No. Sho 62-296,008/1987), and as to zirconium or hafnium compounds, dimethylsilylbis(cyclopentadienyl)zirconium or hafnium dichloride has been synthesized (Z. Naturforsch, 38b, 321–325 (1983) and Inorg. Chem. 1985, 24, 2539).

Further, as to preparation examples of transition-metal compounds having a ligand using substituted-cyclopentadienyl rings crosslinked with silicon, dimethylsilylbis(methylcyclopentadienyl)titanium dichloride (Monatsh. Chem. 112,887–897 (1981)), dimethylsilylbis(t-butylcyclopentadienyl)scandium hydride (J. Am. Chem. Soc. 1988, 110,976–978), Me$_2$Si(-Me$_4$C$_5$)MCH[SiMe$_3$]$_2$ (M=Nd, Sm, Lu) type compounds (J. Am. Chem. Soc. 1985, 107, 8103–8110), etc. have been known.

However, with regard to zirconium compound or titanium compound, an example of those having a dimethylsilylbis(tetramethylcyclopentadienyl)ligand has been known (Chem. Ber. 119, 1750–1754 (1986)), but preparation example of compounds having a ligand using other substituted-cyclopentadienyl rings crosslinked with silicon or germanium has never been reported. Much less, any concrete practical example wherein olefins are polymerized using such compounds to obtain isotactic polymers has also never been reported.

SUMMARY OF THE INVENTION

The present inventors have made extensive research in order to solve the above-mentioned problem and as a result have succeeded in preparing the above-mentioned novel zirconium compound or hafnium compound with a good efficiency, and also have confirmed by polymerization experiments that these compounds are useful as a catalyst component for stereoregular olefin polymerization.

As apparent from the foregoing, the object of the present invention is to provide the above-mentioned novel and useful compounds and their use applications.

The present invention resides in (1) a transition-metal compound expressed by the formula (I)

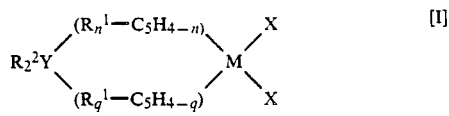

wherein M represents zirconium or hafnium; Y represents silicon or germanium; $R^1_n$-C$_5$H$_{4-n}$ and $R^1_q$-C$_5$H$_{4-q}$ each represent an unsubstituted or substituted cyclopentadienyl group; n and q each represent an integer of 0 to 4, but cases of n=q=0 and n=q=4 are excluded; the respective R$^1$s may be the same or different and each represent hydrogen atom, silyl group or a hydrocarbon radical; the respective R$^2$s may be the same or different and each represent hydrogen atom or a hydrocarbon radical; and the respective Xs may be the same or different and each represent hydrogen atom, a halogen atom or a hydrocarbon radical; and (2) a catalyst for producing a stereoregular olefin polymer, which catalyst comprises as its effective components, (A) a transition-metal compound expressed by the formula

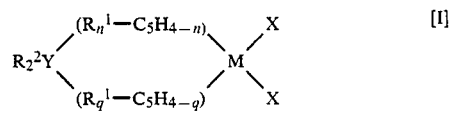

wherein M represents a transition-metal compound of zirconium or hafnium; Y represents silicon or germanium; $R^1_n$-C$_5$H$_{4-n}$ and $R^1_q$-C$_5$H$_{4-q}$ each represent an unsubstituted or substituted cyclopentadienyl group; n and q each represent an integer of 0 to 4, but cases of n=q=0 and n=q=4 are excluded; the respective R$^1$s may be same or different and each represent hydrogen atom, a silyl group or a hydrocarbon radical, but the site of R$^1$ on the cyclopentadienyl ring and the kind of R$^1$ should take a configuration wherein any symmetry plane containing M is absent; the respective R$^2$s may be the same or different and each represent hydrogen atom or a hydrocarbon radical; and the respective Xs may be the same or different and each represent hydrogen atom, a halogen atom or a hydrocarbon radical, and (B) an aluminoxane expressed by the formula [II] or the formula [III]

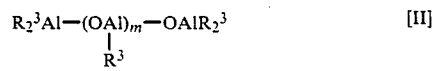

wherein m represents an integer of 4 to 30 and R$^3$ represents a hydrocarbon radical.

Figure 1:
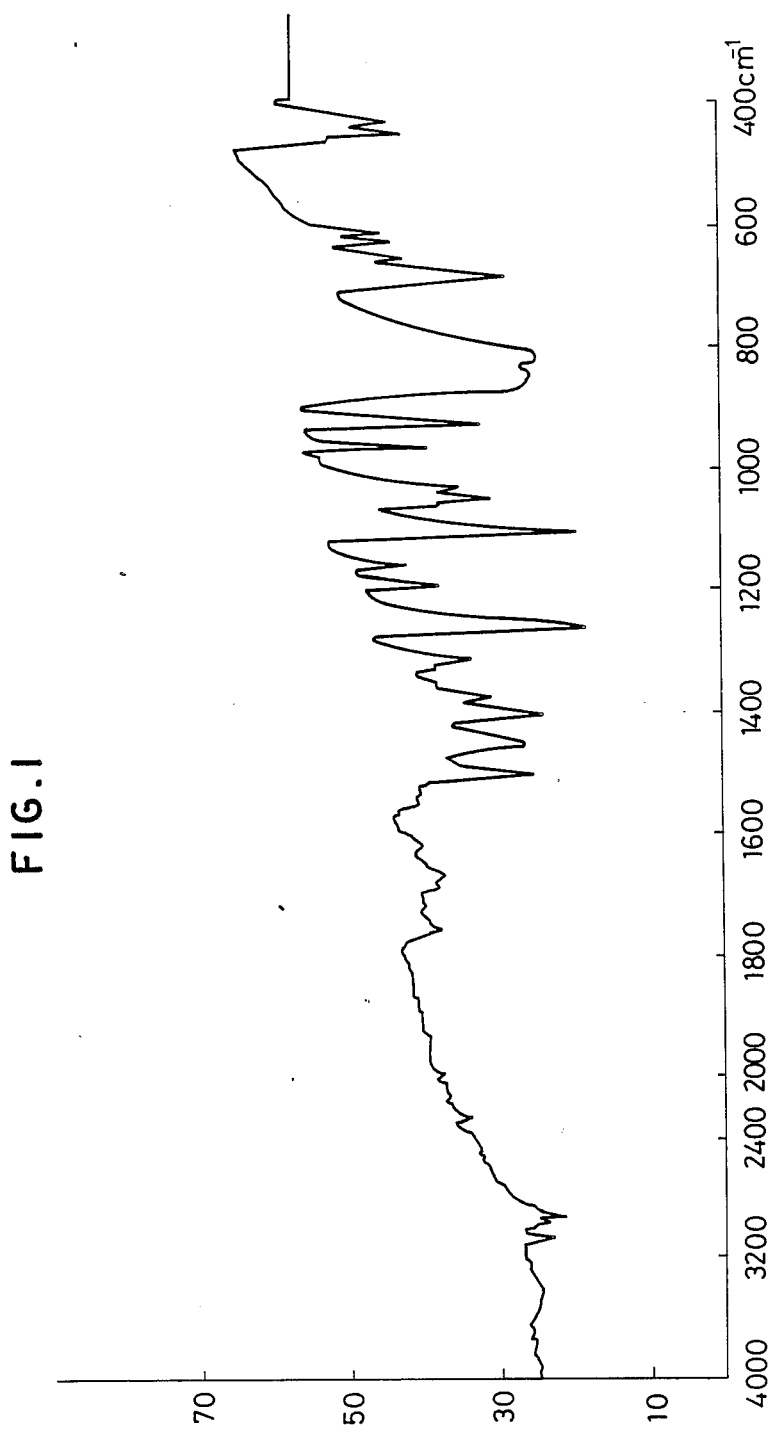
FIGS. 1, 3, 5, 7, 9, 11, 13 and 15 respectively show the IR spetra of the following compounds and FIGS. 2, 4, 6, 8, 10, 12, 14 and 16 respectively show the NMR spectra of the following compounds.
Figure 2:
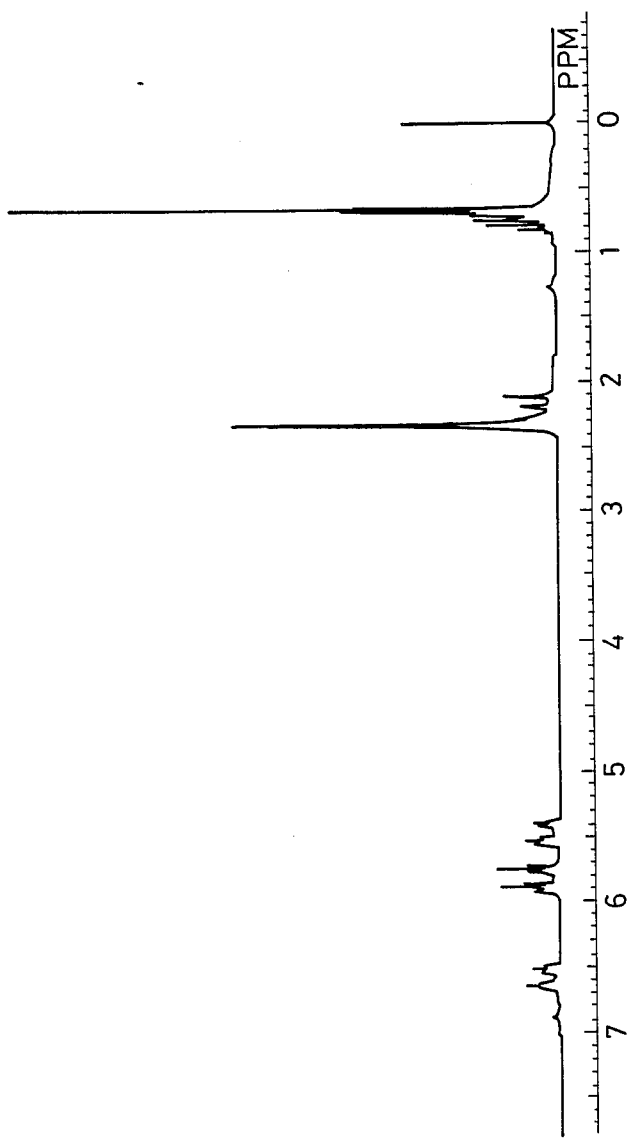
Figure 3:
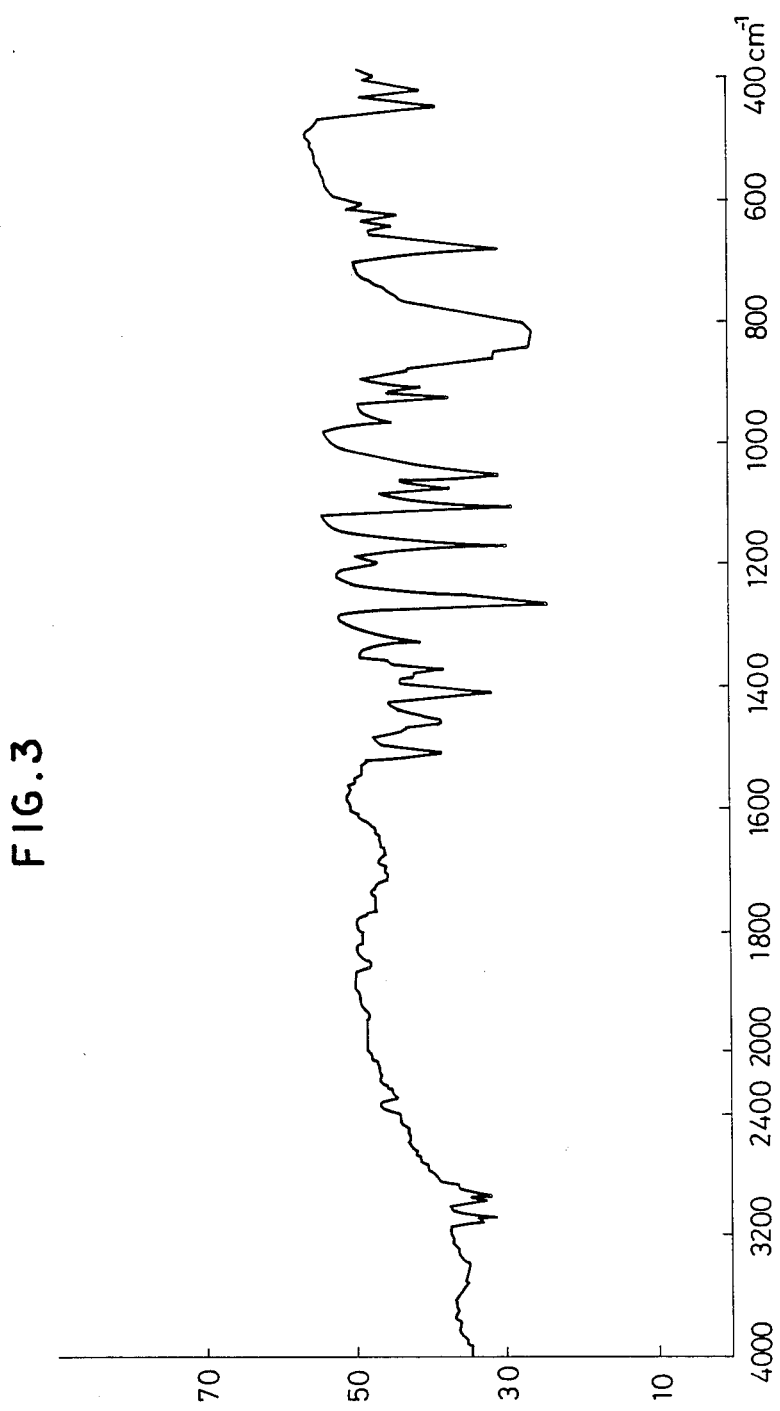
Figure 4:
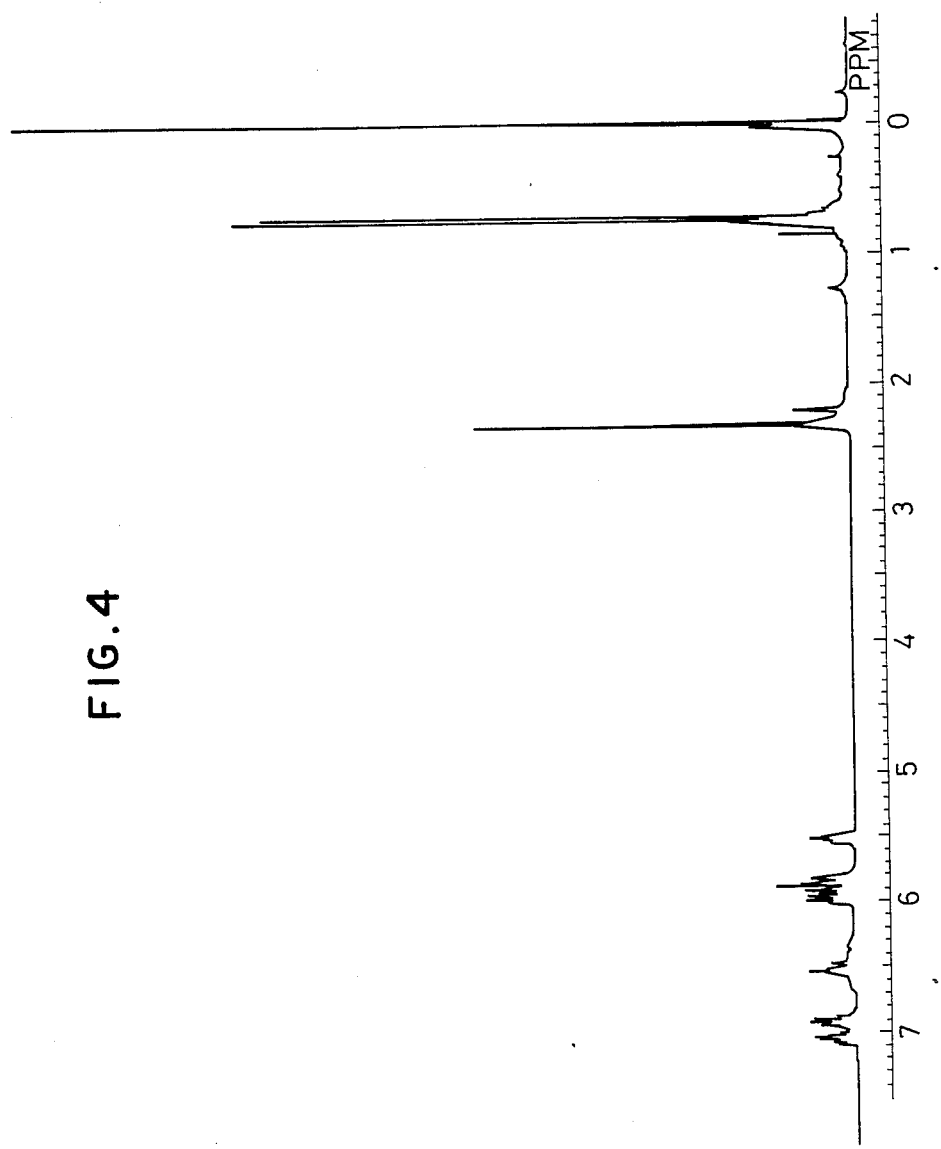
Figure 5:
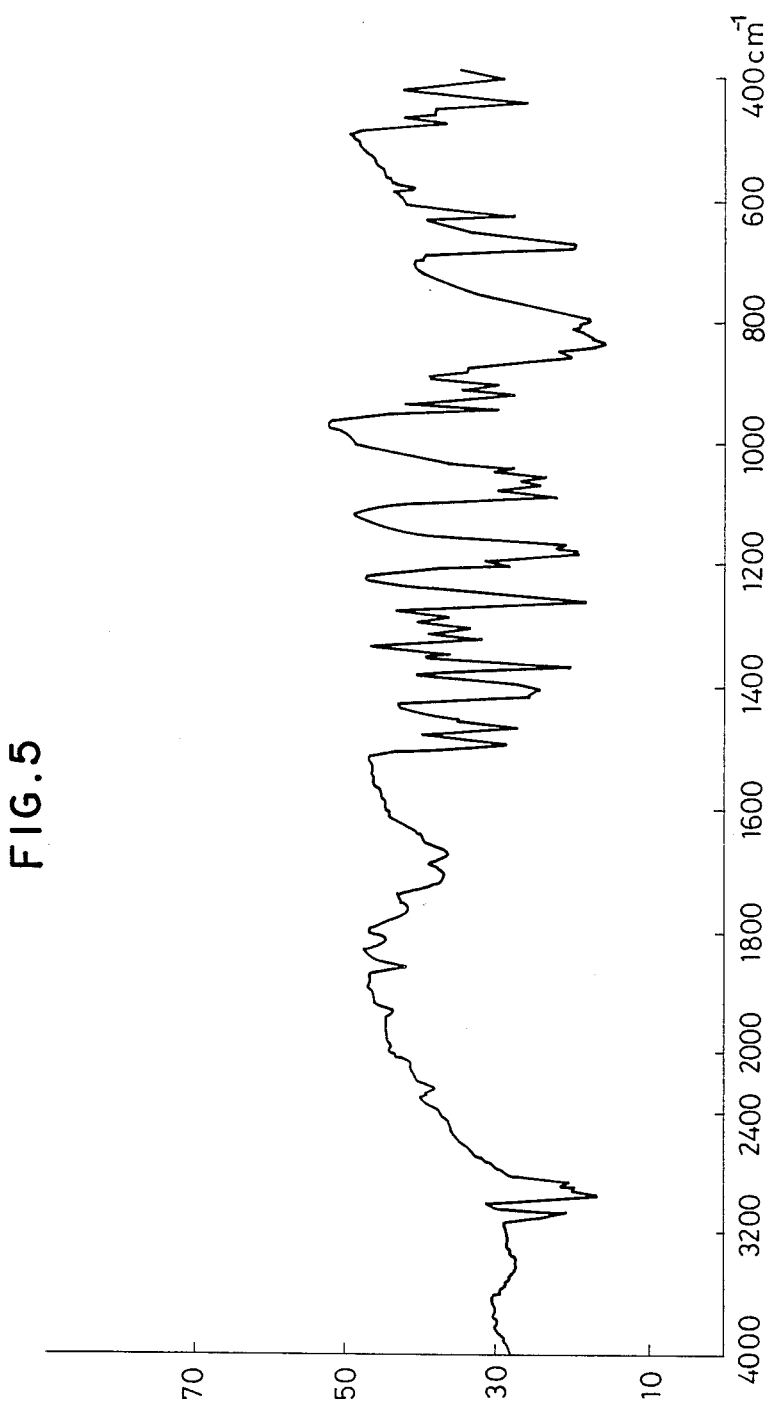
Figure 6:
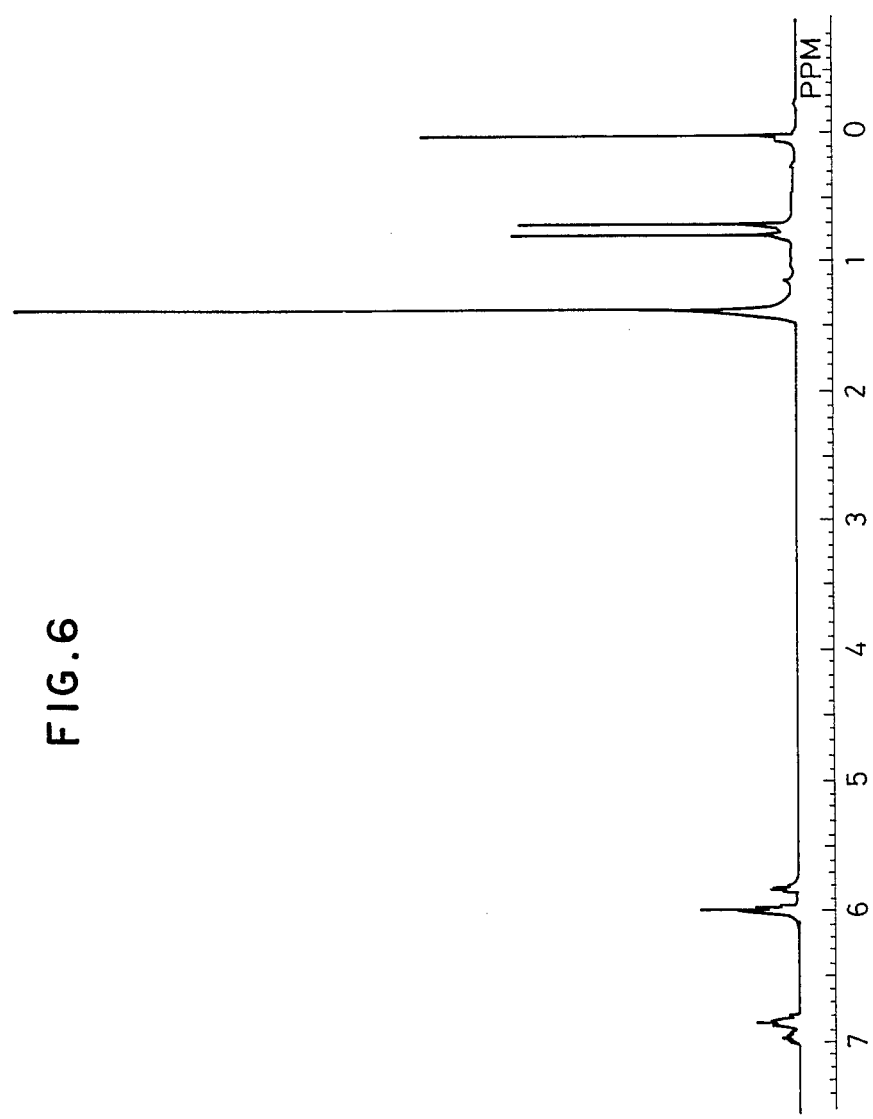
Figure 7:
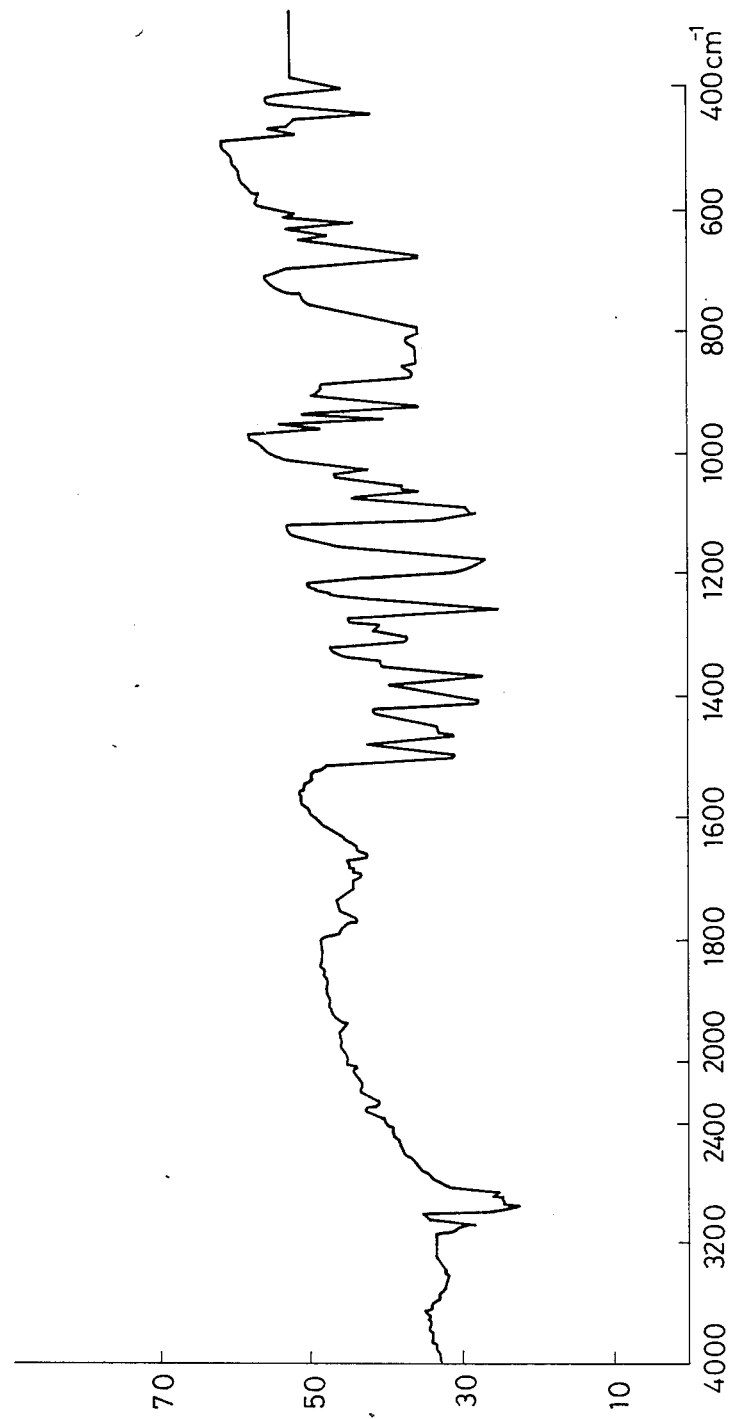
Figure 8:
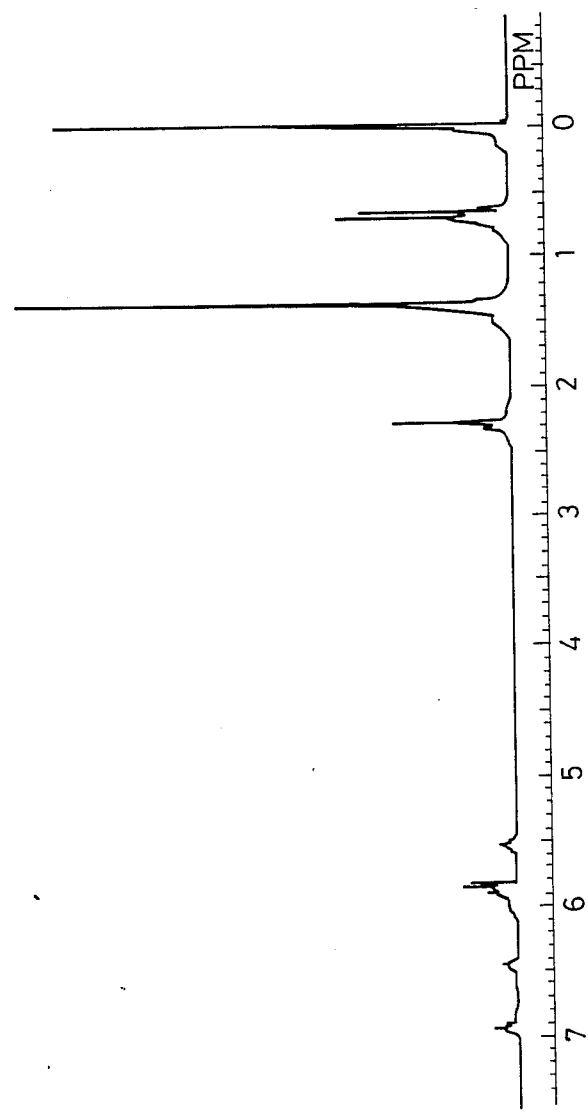
Figure 9:
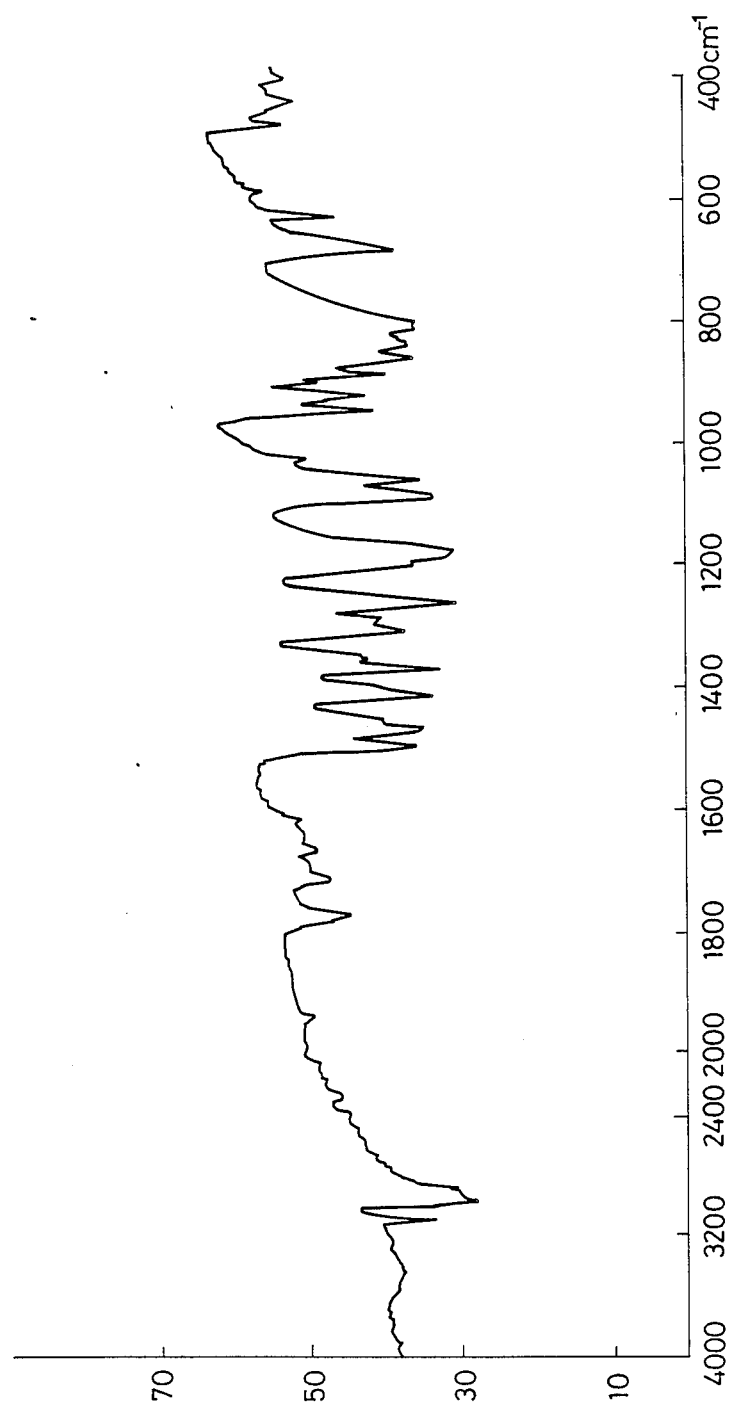
Figure 10:
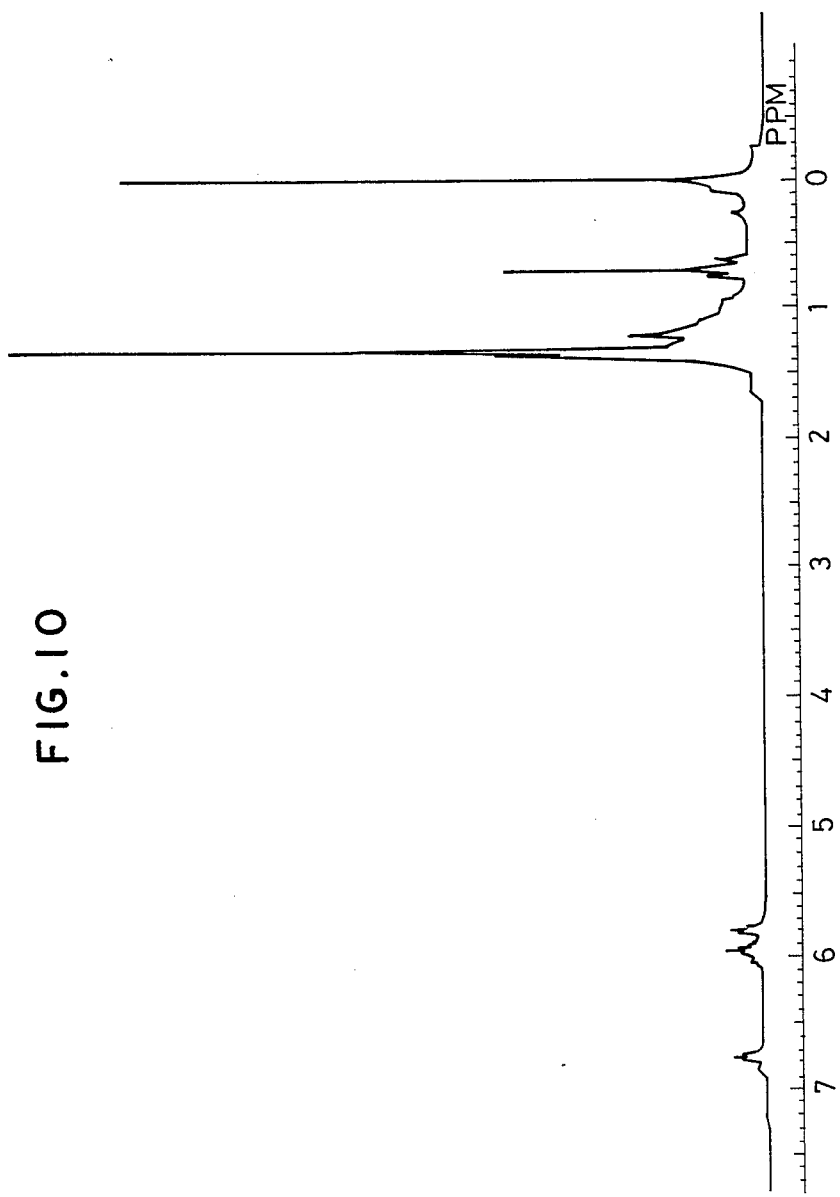
Figure 11:
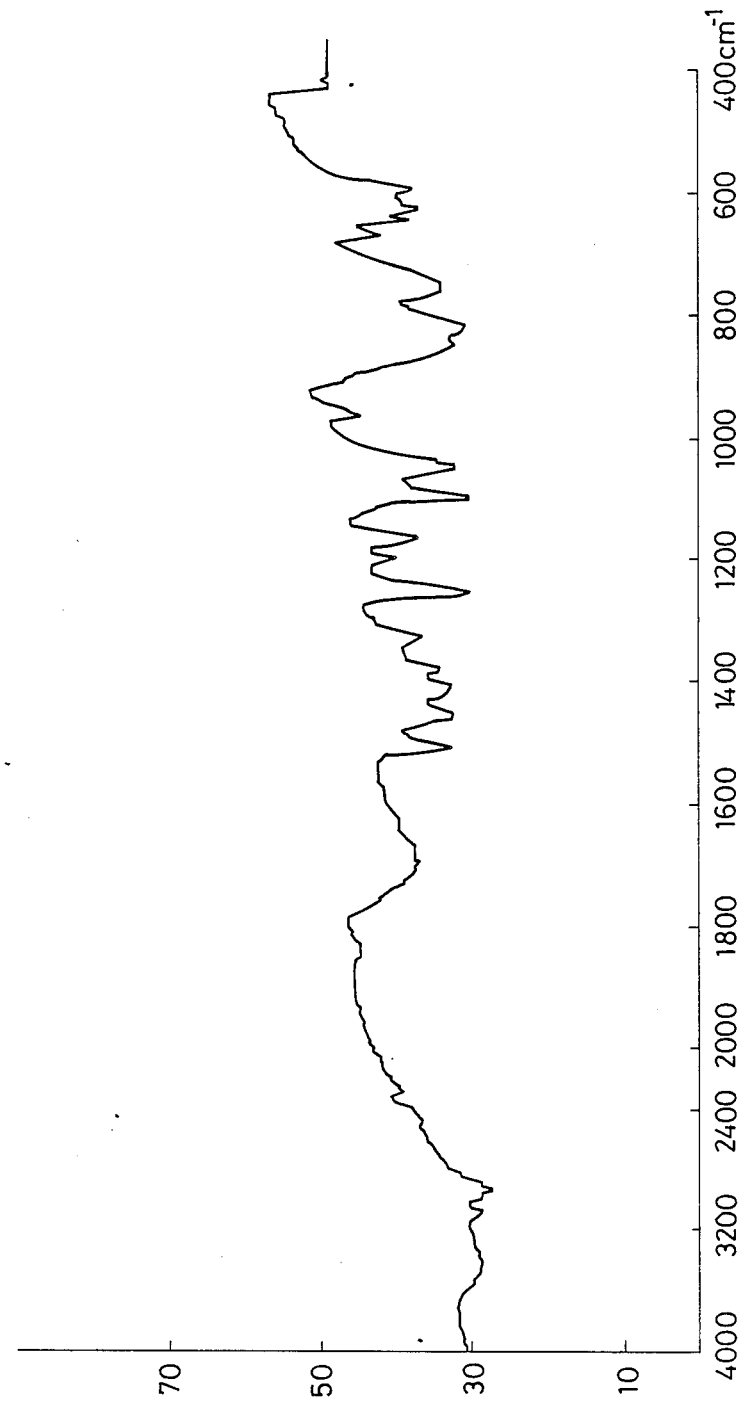
Figure 12:
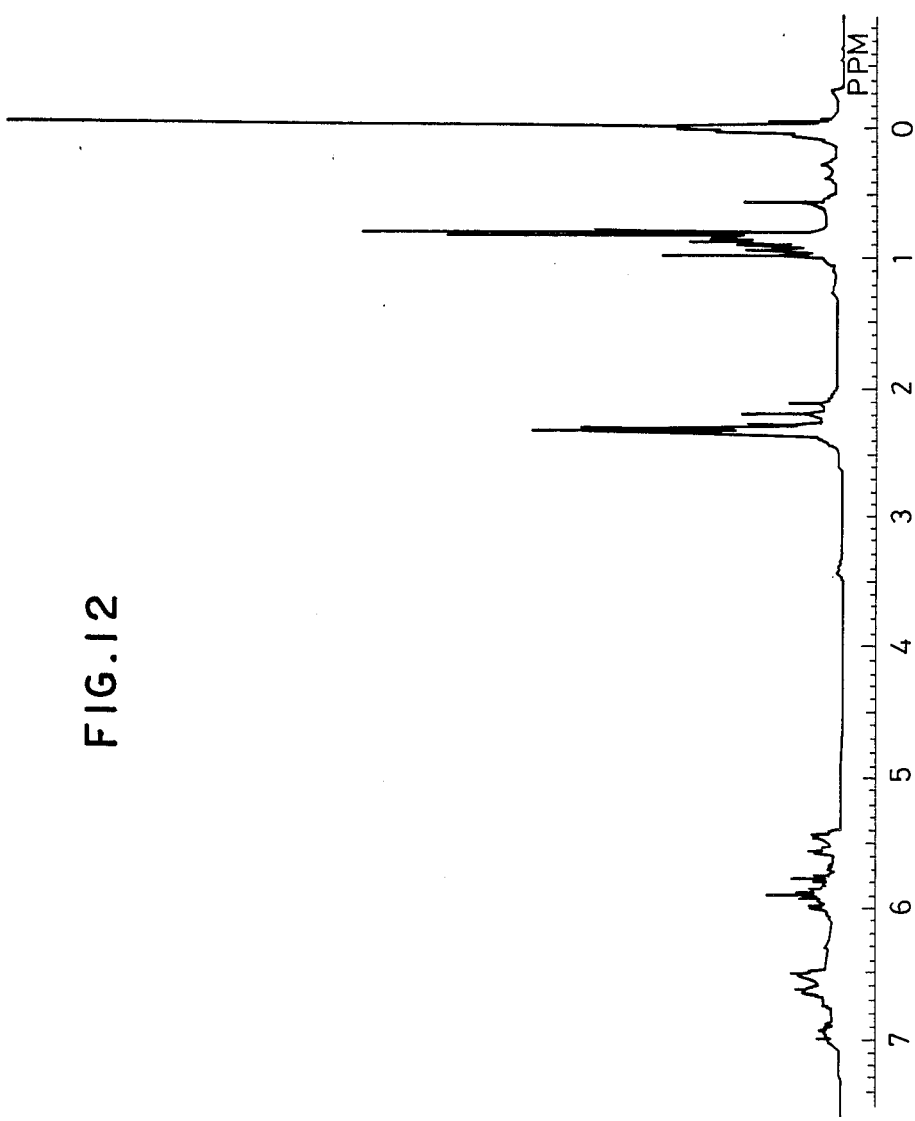
Figure 13:
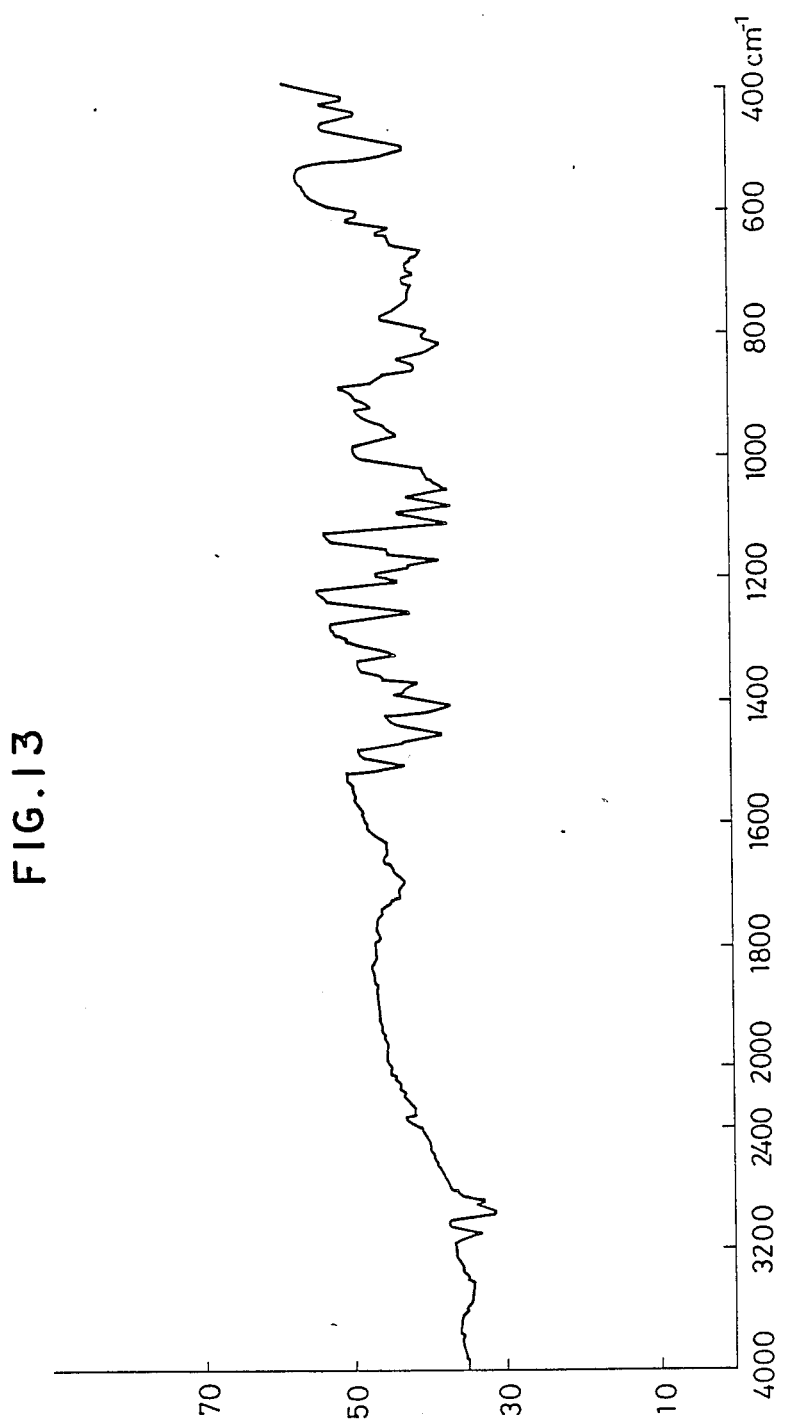
Figure 14:
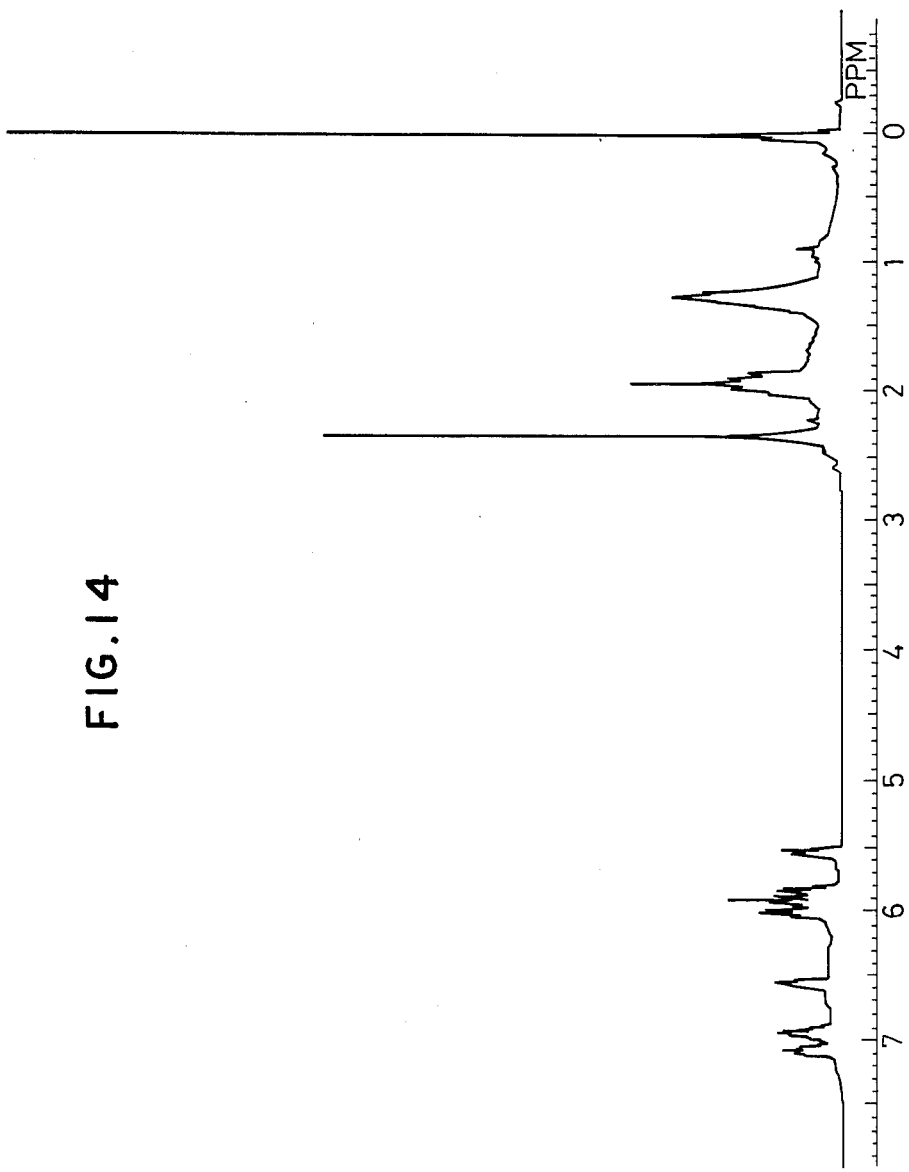
Figure 15:
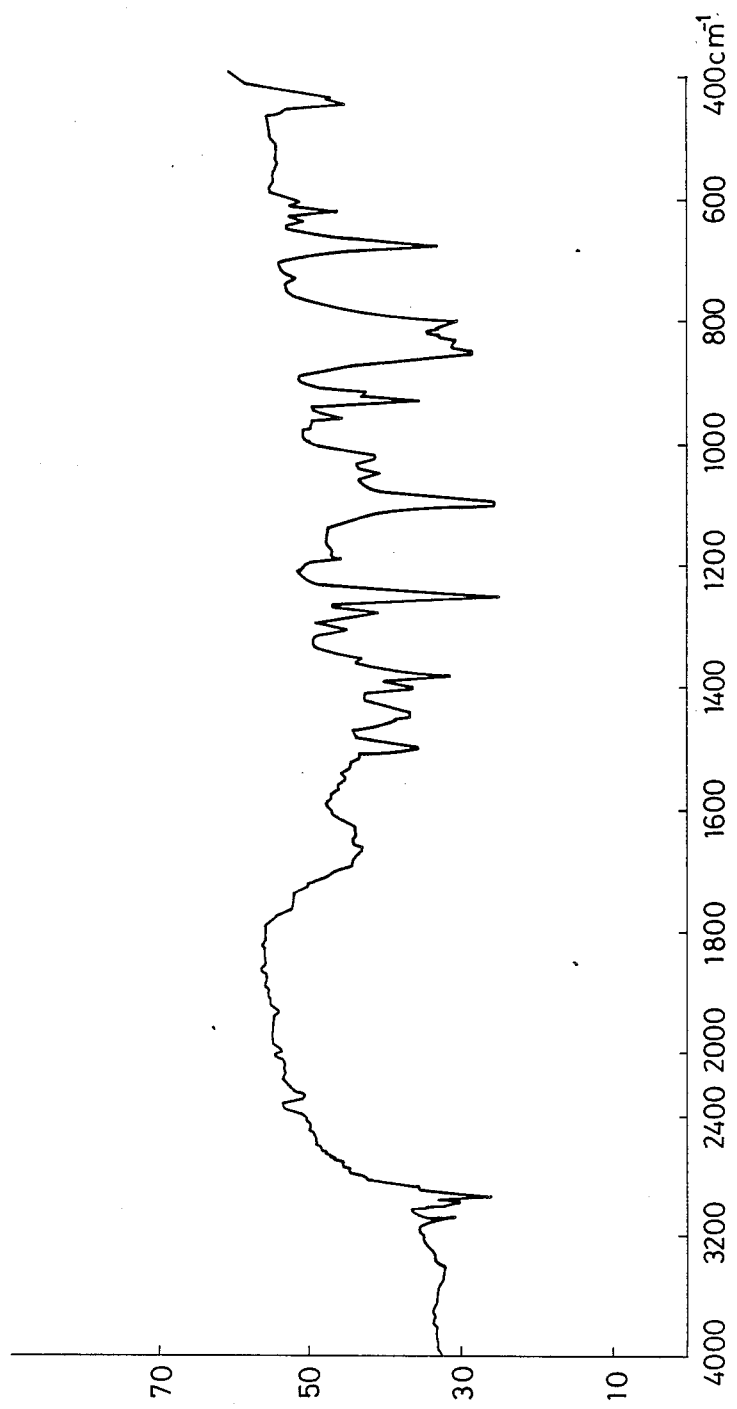
Figure 16:
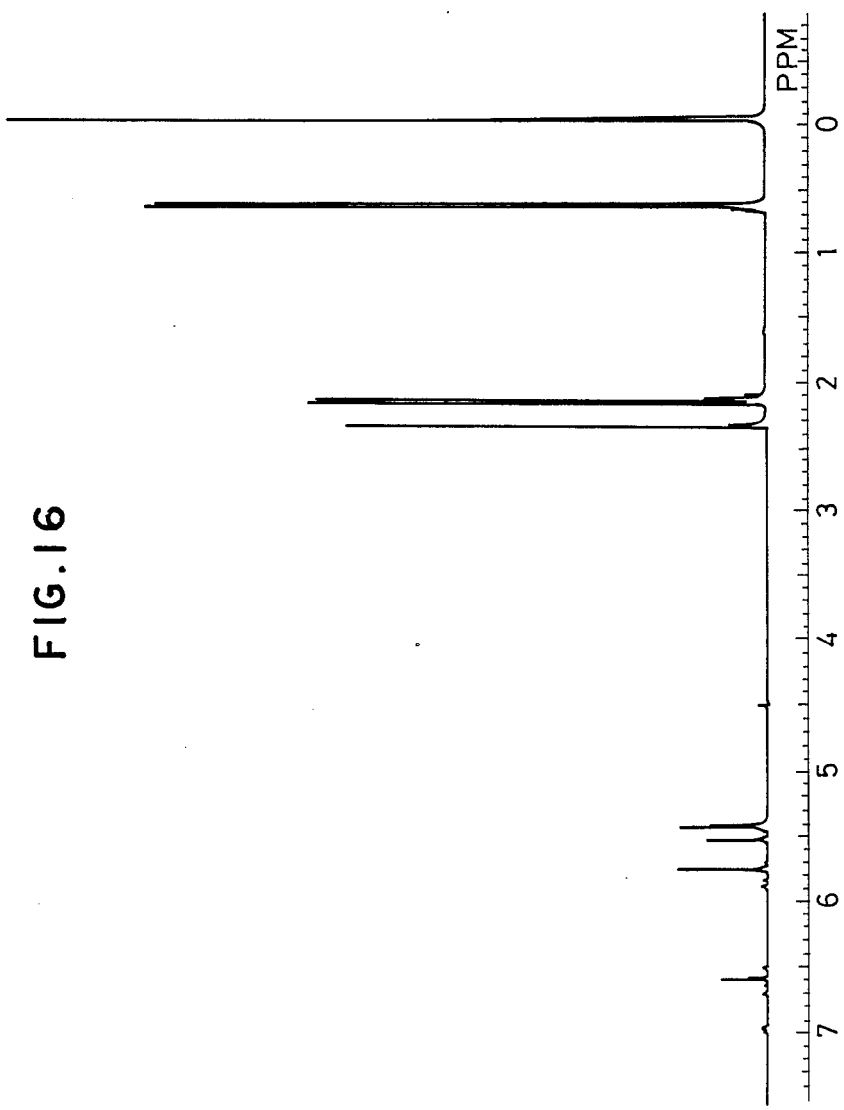

| Zirconium compound | IR spectra | NMR spectra |
| --- | --- | --- |
| $Me_2Si(Me-C_5H_3)_2ZrCl_2$ | FIG. 1 | FIG. 2 |
| $Me_2Si(C_5H_4)(Me-C_5H_3)ZrCl_2$ | FIG. 3 | FIG. 4 |
| $Me_2Si(C_5H_4)(t-Bu-C_5H_3)ZrCl_2$ | FIG. 5 | FIG. 6 |
| $Me_2Si(Me-C_5H_3)(t-Bu-C_5H_3)ZrCl_2$ | FIG. 7 | FIG. 8 |
| $Me_2Si(t-Bu-C_5H_3)_2ZrCl_2$ | FIG. 9 | FIG. 10 |
| $Me_2Ge(Me-C_5H_3)_2ZrCl_2$ | FIG. 11 | FIG. 12 |
| $(CH_2)_4Si(C_5H_4)(Me-C_5H_3)ZrCl_2$ | FIG. 13 FIG. 14 | |
| $Me_2Si(Me-C_5H_3)(Me_2-C_5H_2)ZrCl_2$ | FIG. 15 | FIG. 16 |

Figure 17:
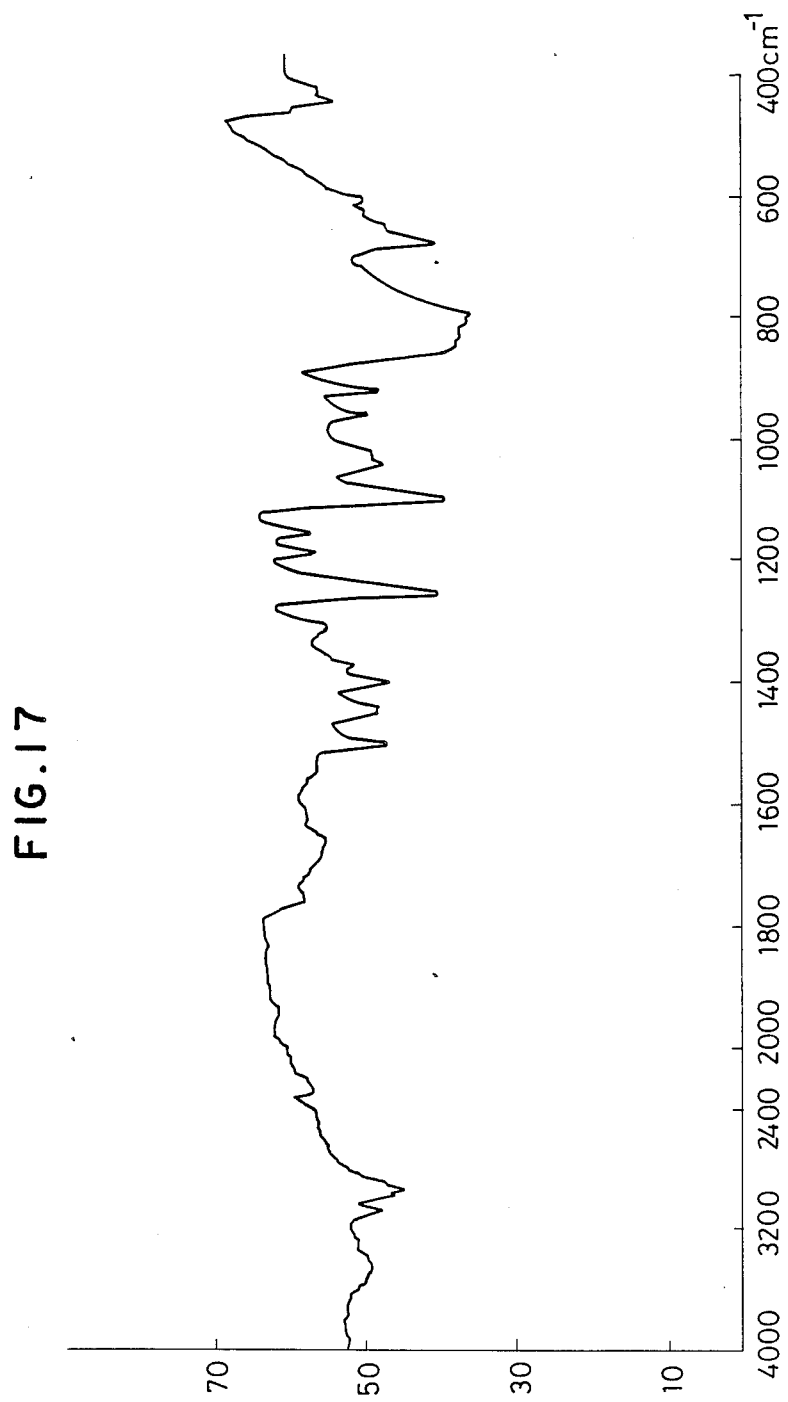
Figure 18:
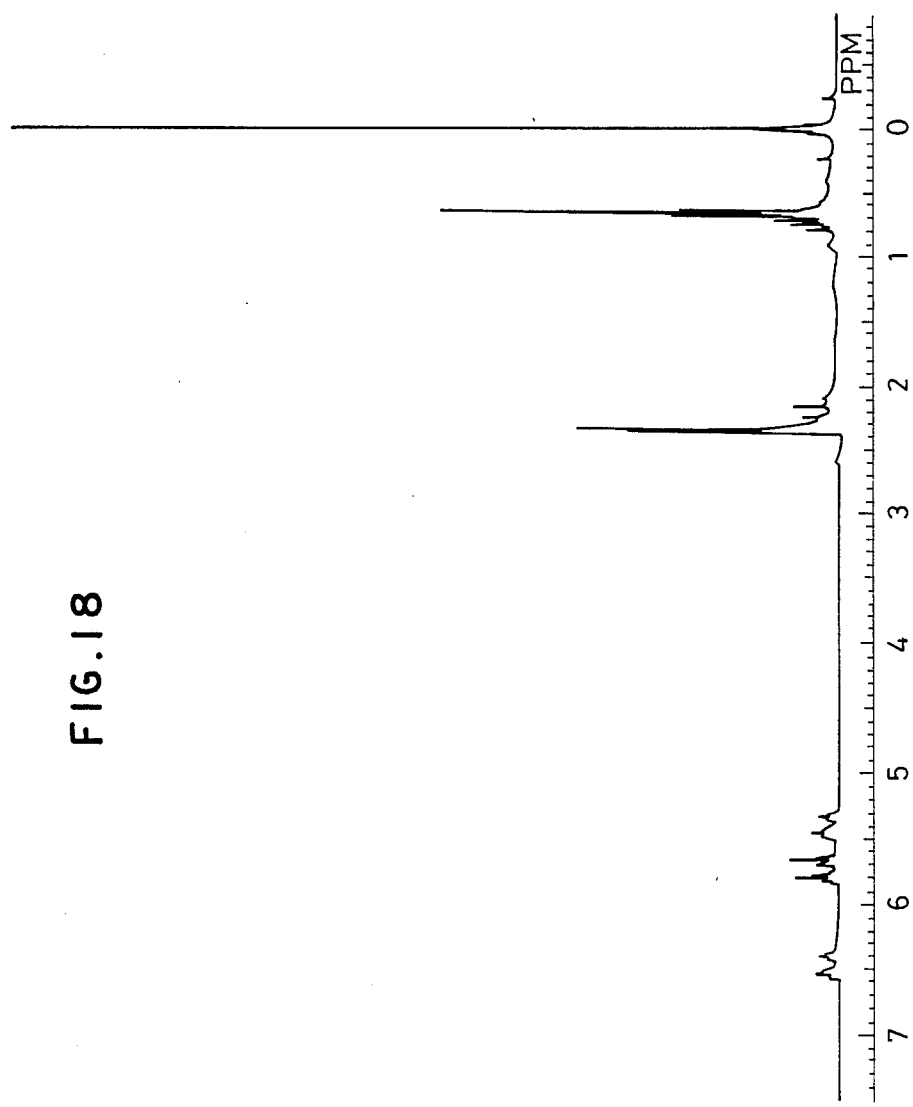
Figure 19:
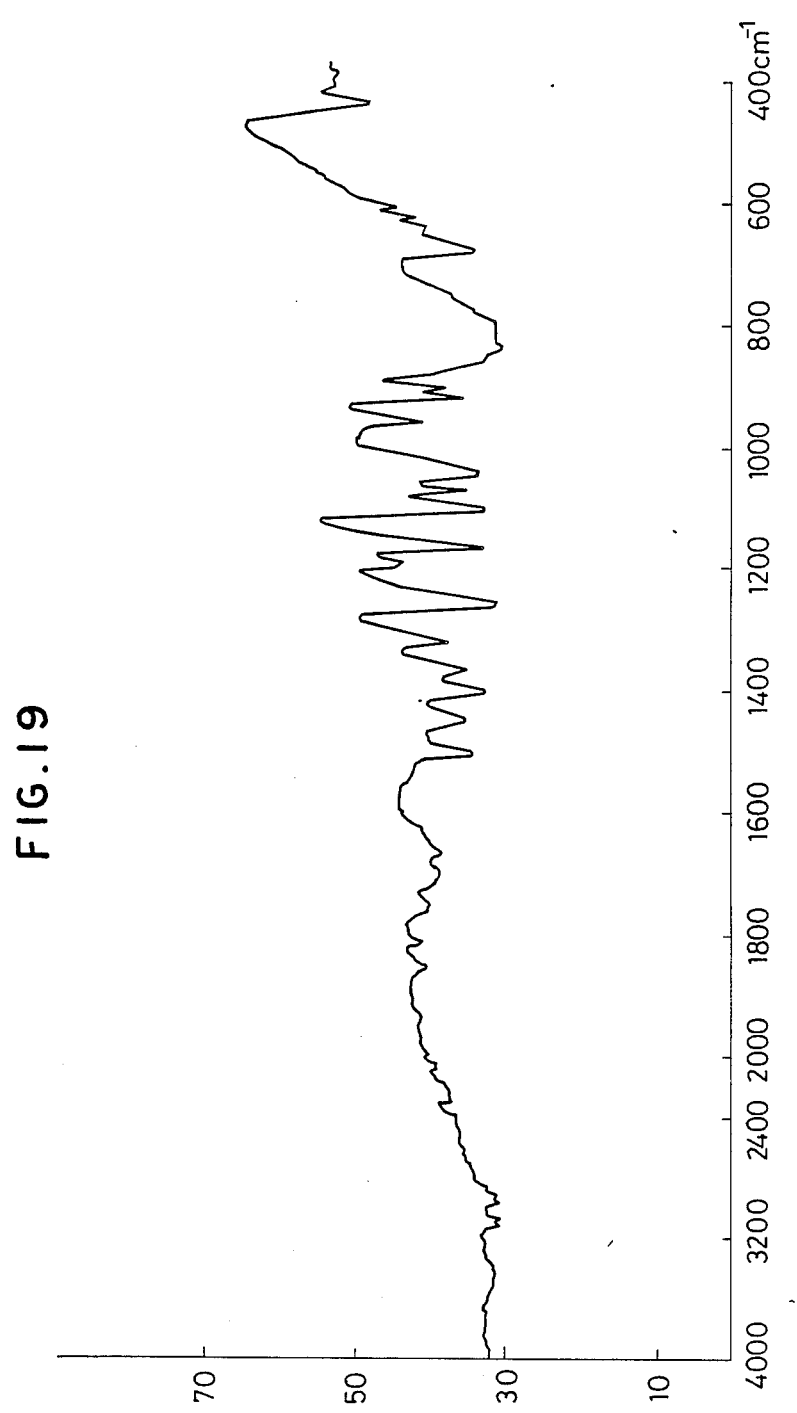
Figure 20:
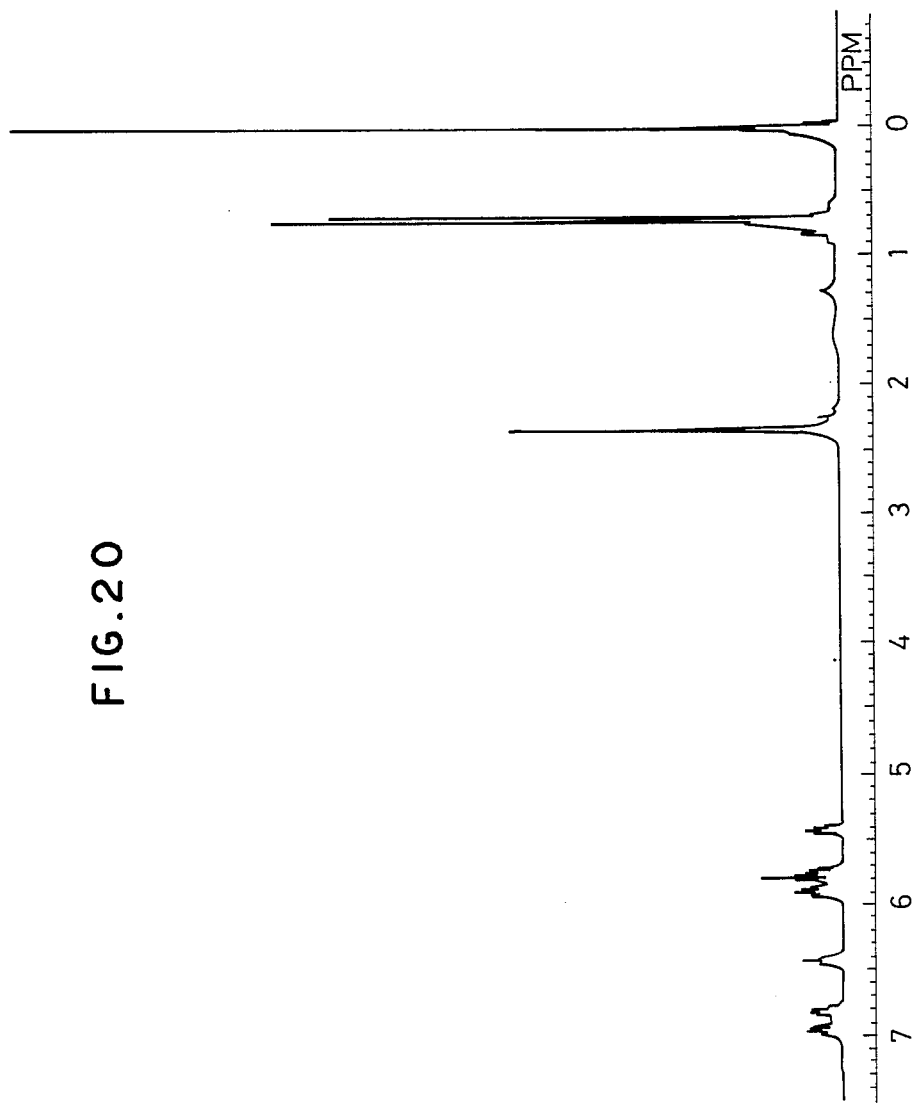
Figure 21:
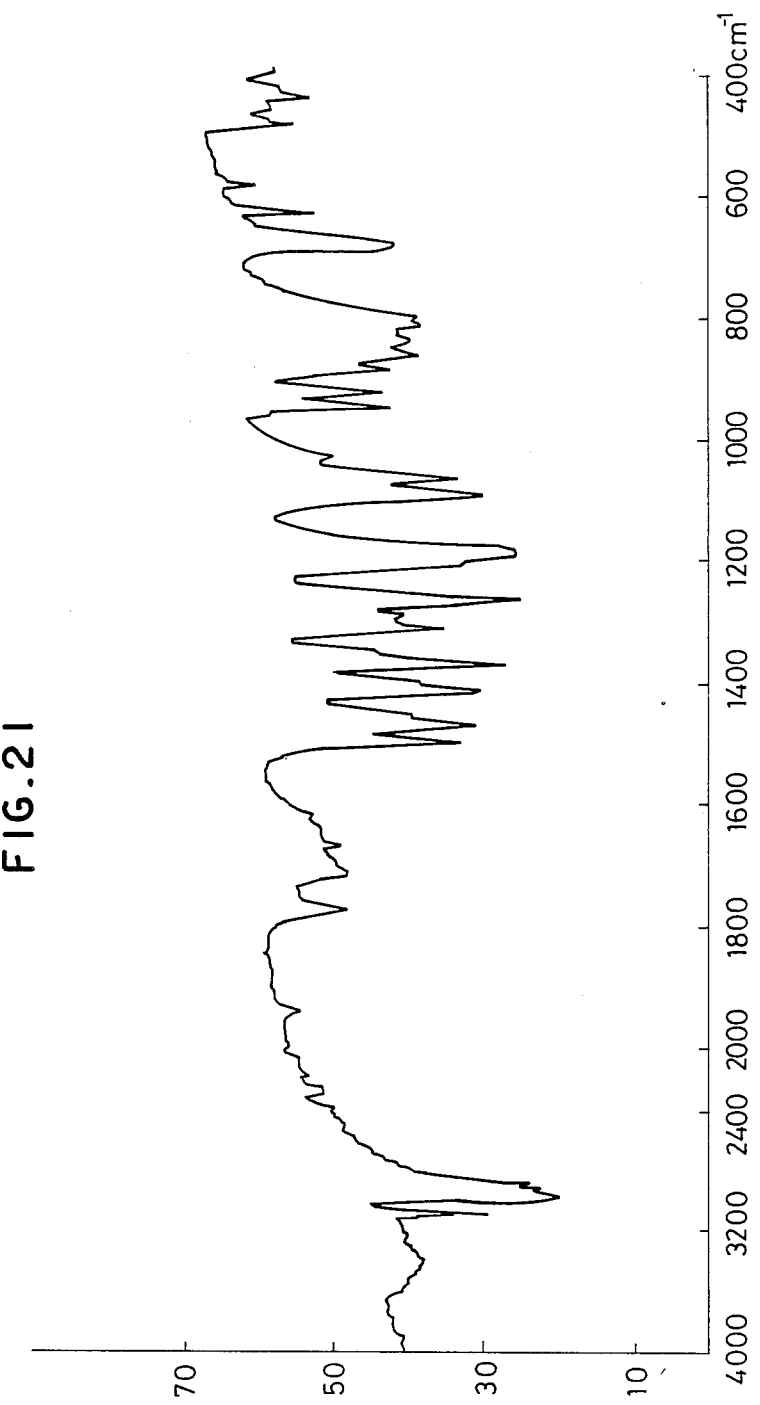
Figure 22:
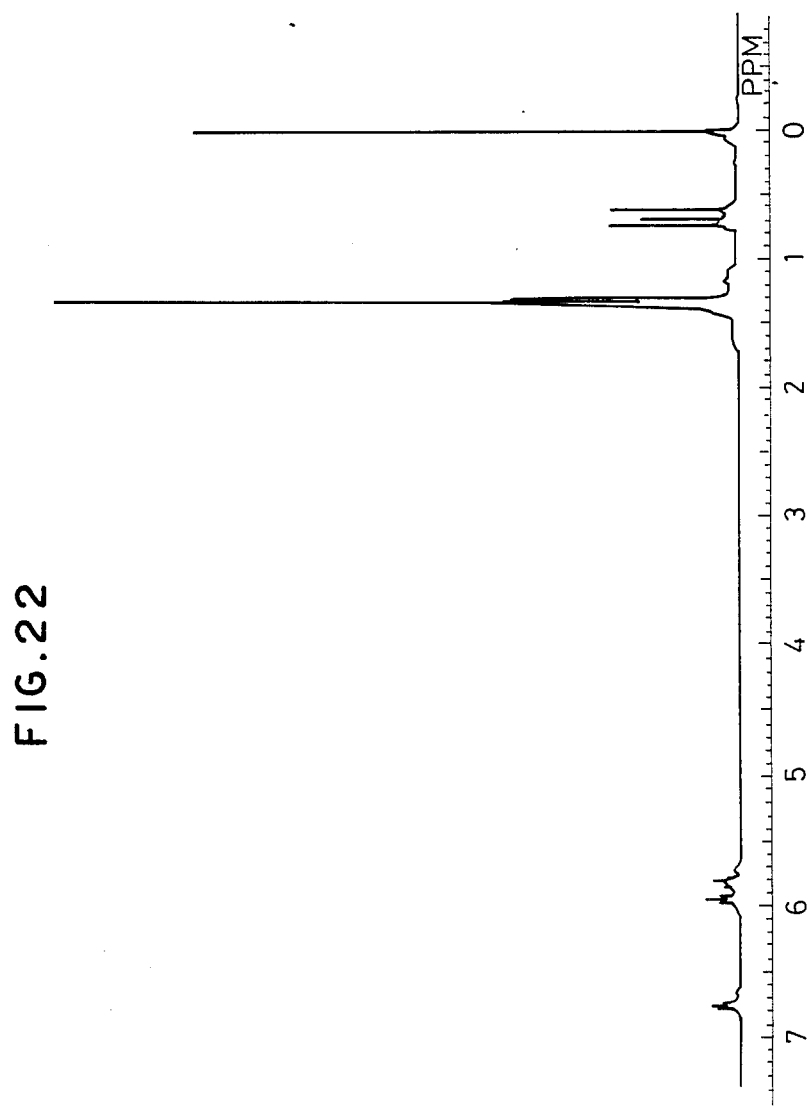

FIGS. 17, 19 and 21 respectively show the IR spectra of the following compounds and FIGS. 18, 20 and 22 respectively show the NMR spectra of the following compounds:

| Hafnium compound | IR spectra | NMR spectra |
| --- | --- | --- |
| $Me_2Si(Me-C_5H_3)_2HfCl_2$ | FIG. 17 | FIG. 18 |
| $Me_2Si(C_5H_4)(Me-C_5H_3)HfCl_2$ | FIG. 19 | FIG. 20 |
| $Me_2Si(t-Bu-C_5H_3)_2HfCl_2$ | FIG. 21 | FIG. 22 |

FIG. 23 shows a flowsheet illustrating the polymerization step of the catalyst of the present invention.

DETAILED DESCRIPTION OF PREFERRED EMBODIMENTS

The compound [I] of the present invention is a novel zirconium or hafnium compound having a bidentate ligand of bis-substituted-cyclopentadienyl rings having a bridged structure. The compound includes those of racemic form and meso form depending on the steric configuration of substituents on two cyclopentadienyl rings and may have either of the structures. Further, those obtained by mixing the two in an optional proportion may also be included.

In the zirconium or hafnium compound of the present invention, Y in the formula [I] is silicon or germanium. The number of the substituents on the respective cyclopentadienyl rings may be any of zero to 4, but at least one of the cyclopentadienyl rings is required to have substituent(s) and also a case where the cyclopentadienyl rings both have 4 substituents is excluded. The respective $R^1$s may be the same or different and each represent hydrogen atom, a silyl group or a hydrocarbon radical such as alkyl, alkenyl, aryl, alkylaryl, arylalkyl, etc. each of 1 to 20 carbon atoms.

Examples of the silyl group are trimethylsilyl group, triethylsilyl group, triphenylsilyl group, etc. Examples of the hydrocarbon radical are methyl group, ethyl group, propyl group, isopropyl group, butyl group, sec-butyl group, tert-butyl group, pehnyl group, tolyl group, biphenyl group, naphthyl group, etc. The respective $R^2$s may be the same or different and each represent hydrogen atom or the above hydrocarbon radical. The respective $X^2$s may be the same or different and each represent hydrogen atom, a halogen atom such as F, Cl, Br, I, etc. or a hydrocarbon radical mentioned above.

As to representative preparation routes of the compound [I] of the present invention, the following (1) or (2) may be briefly illustrated for example in the case of $n=q=1$, but the routes are not limited to these two: (1) a case where the substituents of the cyclopentadienyl rings are the same:

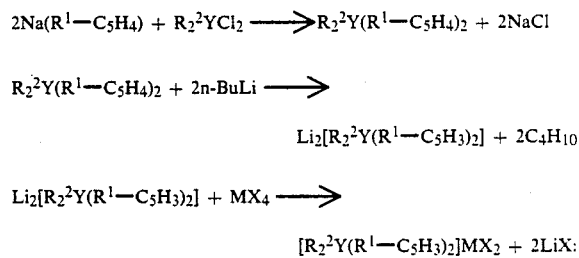

(2) a case where the substituents of the cyclopentadienyl rings are different:

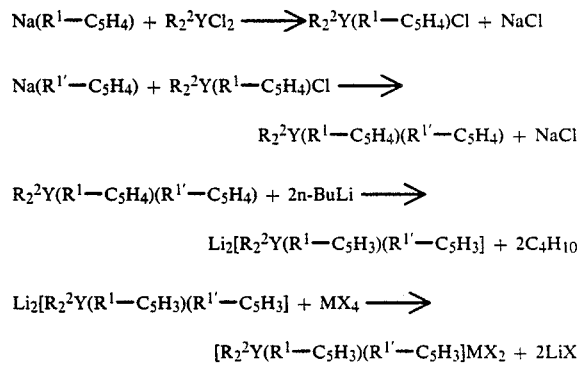

Preparation of a bidentate ligand of bis-substituted-cyclopentadienyl rings having a bridged structure (e.g. compounds $R_2^2Y(R^1-C_5H_4)_2$ or $R_2^2Y(R^1-C_5H_4)(R^{1'}-C_5H_4)$ in the above preparation routes (1) or (2)) has been known (see Monatsh. Chem. 112,887-897 (1981), J. Am. Chem. Soc. 1988, 110,976-978, J. Am. Chem. Soc. 1985, 107, 8103-8110, etc.)

As to such a bidentate ligand, the starting material may be converted with an alkyllithium into a lithium compound, followed by using it for the subsequent reaction. Further, it is also possible to use it in the form of a potassium compound or a sodium compound.

The reaction of $MX_4$ with a Li compound (e.g. compounds expressed by $Li_2[R_2^2Y(R^1-C_5H_3)_2]$ or $Li_2[R_2^2Y(R^1-C_5H_3)(R^{1'}-C_5H_3)]$ in the above preparation routes (1) and (2)) may be carried out in an ether, preferably tetrahydrofuran (THF) as a reaction solvent. The reaction is preferred to be carried out in a molar ratio of Li compound/$MX_4$ within a range of 1.0 to 1.5, particularly 1.0 to 1.1. The reaction temperature is preferred to be in a range of $-80°$ to $+100°$ C., particularly 0° to 70° C. The thus formed compound [I] may be purified by recrystallization.

Non-limitative examples of the above-mentioned transition-metal compounds are as follows:

Zirconium Compounds dimethylsilylbis(methylcyclopentadienyl)zirconium dichloride, diphenylsilylbis(methylcyclopentadienyl)zirconium dichloride, cyclotrimethylenesilylbis(methylcyclopentadienyl)zirconium dichloride,
cyclotetramethylenesilylbis(methylcyclopentadienyl)zirconium dichloride,
cyclopentamethylenesilylbis(methylcyclopentadienyl)zirconium dichloride,
dimethylsilylbis(methylcyclopentadienyl)zirconium dibromide,
dimethylsilylbis(methylcyclopentadienyl)zirconium methyl chloride,
dimethylsilylbis(methylcyclopentadienyl)zirconium dimethyl,
dimethylsilylbis(methylcyclopentadienyl)zirconium diphenyl,
dimethylsilylbis(ethylcyclopentadienyl)zirconium dichloride,
dimethylsilylbis(isopropylcyclopentadienyl)zirconium dichloride,
dimethylsilylbis(t-butylcyclopentadienyl)zirconium dichloride,
dimethylsilylbis(phenylcyclopentadienyl)zirconium dichloride,
dimethylsilylbis(trimethylsilylcyclopentadienyl)zirconium dichloride,
dimethylsilyl(cyclopentadienyl)(methylcyclopentadienyl)zirconium dichloride,
diphenylsilyl(cyclopentadienyl)(methylcyclopentadienyl)zirconium dichloride,
cyclotetramethylenesilyl(cyclopentadienyl)(methylcyclopentadienyl)zirconium dichloride,
dimethylsilyl(cyclopentadienyl)(methylcyclopentadienyl)zirconium dimethyl,
dimethylsilyl(cyclopentadienyl)(methylcyclopentadienyl)zirconium diphenyl,
dimethylsilyl(cyclopentadienyl)(isopropylcyclopentadienyl)zirconium dichloride,
dimethylsilyl(cyclopentadienyl)(t-butylcyclopentadienyl)zirconium dichloride,
dimethylsilyl(cyclopentadienyl)(phenylcyclopentadienyl)zirconium dichloride,
dimethylsilyl(cyclopentadienyl)(trimethylsilylcyclopentadienyl)zirconium dichloride,
dimethylsilyl(methylcyclopentadienyl)(phenylcyclopentadienyl)zirconium dichloride,
dimethylsilyl(methylcyclopentadienyl)(t-butylcyclopentadienyl)zirconium dichloride,
dimethylgermylbis(methylcyclopentadienyl)zirconium dichloride,
dimethylgermylbis(t-butylcyclopentadienyl)zirconium dichloride,
dimethylgermylbis(phenylcyclopentadienyl)zirconium dichloride,
dimethylgermyl(cyclopentadienyl)(methylcyclopentadienyl)zirconium dichloride,
dimethylgermyl(cyclopentadienyl)(phenylcyclopentadienyl)zirconium dichloride,
dimethylgermyl(cyclopentadienyl)(t-butylcyclopentadienyl)zirconium dichloride,
dimethylsilyl(methylcyclopentadienyl)(dimethylcyclopentadienyl)zirconium dichloride,
dimethylgermyl(methylcyclopentadienyl)(dimethylcyclopentadienyl)zirconium dichloride, etc.

Hafnium Compounds dimethylsilylbis(methylcyclopentadienyl)hafnium dichloride,
diphenylsilylbis(methylcyclopentadienyl)hafnium dichloride,
cyclotrimethylenesilylbis(methylcyclopentadienyl)hafnium dichloride,
cyclotetramethylenesilylbis(methylcyclopentadienyl)hafnium dichloride,
cyclopentamethylenesilylbis(methylcyclopentadienyl)hafnium dichloride,
dimethylsilylbis(methylcyclopentadienyl)hafnium dibromide,
dimethylsilylbis(methylcyclopentadienyl)hafnium methyl chloride,
dimethylsilylbis(methylcyclopentadienyl)hafnium dimethyl,
dimethylsilylbis(methylcyclopentadienyl)hafnium diphenyl,
dimethylsilylbis(ethylcyclopentadienyl)hafnium dichloride,
dimethylsilylbis(isopropylcyclopentadienyl)hafnium dichloride,
dimethylsilylbis(t-butylcyclopentadienyl)hafnium dichloride,
dimethylsilylbis(phenylcyclopentadienyl)hafnium dichloride,
dimethylsilylbis(trimethylsilylcyclopentadienyl)hafnium dichloride,
dimethylsilyl(cyclopentadienyl)(methylcyclopentadienyl)hafnium dichloride,
diphenylsilyl(cyclopentadienyl)(methylcyclopentadienyl)hafnium dichloride,
cyclotetramethylenesilyl(cyclopentadienyl)(methylcyclopentadienyl)hafnium dichloride,
dimethylsilyl(cyclopentadienyl)(methylcyclopentadienyl)hafnium dimethyl,
dimethylsilyl(cyclopentadienyl)(methylcyclopentadienyl)hafnium diphenyl,
dimethylsilyl(cyclopentadienyl)(isopropylcyclopentadienyl)hafnium dichloride,
dimethylsilyl(cyclopentadienyl)(t-butylcyclopentadienyl)hafnium dichloride,
dimethylsilyl(cyclopentadienyl)(phenylcyclopentadienyl)hafnium dichloride,
dimethylsilyl(cyclopentadienyl)(trimethylsilylcyclopentadienyl)hafnium dichloride,
dimethylsilyl(methylcyclopentadienyl)(phenylcyclopentadienyl)hafnium dichloride,
dimethylsilyl (methylcyclopentadienyl)(t-butylcyclopentadienyl)hafnium dichloride,
dimethylgermylbis(methylcyclopentadienyl)hafnium dichloride,
dimethylgermylbis(t-butylcyclopentadienyl)hafnium dichloride,
dimethylgermylbis(phenylcyclopentadienyl)hafnium dichloride,
dimethylgermyl(cyclopentadienyl)(methylcyclopentadienyl)hafnium dichloride,
dimethylgermyl(cyclopentadienyl)(phenylcyclopentadienyl)hafnium dichloride,
dimethylgermyl(cyclopentadienyl)(t-butylcyclopentadienyl)hafnium dichloride,
dimethylsilyl(methylcyclopentadienyl)(dimethylcyclopentadienyl)hafnium dichloride,
dimethylgermyl(methylcyclopentadienyl)(dimethylcyclopentadienyl)hafnium dichloride, etc.

The zirconium or hafnium compounds [I] of the pesent invention exhibits a superior olefin polymerization activity in the presence of an aluminoxane and is useful compounds as a polymerization catalyst component. The aluminoxane as one of the catalyst components used in the polymerization is an organic aluminum compound expressed by the formula [II] or the formula [III]

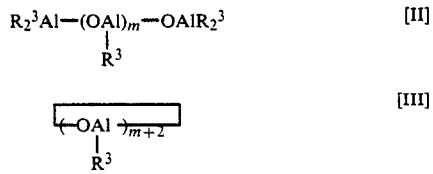

wherein $R^3$ represents a hydrocarbon radical such as methyl group, ethyl group, propyl group, butyl group, etc., preferably methyl group or ethyl group and m represents an integer of 4 to 30, preferably 6 or more, more preferably 10 or more. Preparation of such compounds are known. For example, they may be prepared by adding a trialkylaluminium to a hydrocarbon suspension of a compound containing adsorbed water or a salt containing water of crystallization such as copper sulfate hydrate, aluminum sulfate hydrate, etc., followed by reacting the mixture.

Olefins used for polymerization wherein the catalyst of the present invention is used, are α-olefins such as propylene, 1-butene, 4-methyl-1-pentene, 1-hexene, 1-octene, etc. and mixtures of two or more kinds thereof may also be used for polymerization. Further, it is also possible to copolymerize the above-mentioned α-olefins with ethylene. Still further, the catalyst is effective for copolymerization of α-olefins with conjugated or non-conjugated dienes such as butadiene, 1,4-hexadiene, 1,4-pentadiene, 1,7-octadiene, etc., styrene or cyclic olefins such as cyclopropene, cyclobutene, norbornene, dicyclopentadiene, etc.

As to the polymerization process employed in the present invention, either of liquid phase polymerization or gas phase polymerization is possible. As the polymerization solvent for liquid phase polymerization, hydrocarbons capable of dissolving both the components of the zirconium or hafnium compound and the aluminoxane are used, and concretely, aromatic hydrocarbons such as benzene, toluene, o-xylene, m-xylene, p-xylene, ethylbenzene, butylbenzene, mesitylene, naphthalene, etc., preferably toluene and xylene are used. Further, even in the case of solvents uncapable of dissolving both the components of the zirconium compound or the hafnium compound and the aluminoxane, if prepolymerization is carried out in aromatic hydrocarbons in advance, polymerization can be carried out.

Examples of such solvents are aliphatic hydrocarbons such as butane, isobutane, pentane, hexane, octane, decane, dodecane, hexadecane, octadecane, etc., alicyclic hydrocarbons such as cyclopentane, methylcyclopentane, cyclohexane, cyclooctane, etc., petroleum fractions such as gasoline, kerosine, gas oil, etc. Among these, aliphatic hydrocarbons are preferred. Further, it is also possible to use liquefied olefins themselves such as liquefied propylene, liquefied butene-1, etc.

As to the catalyst components, the mixture of both the components of the zirconium compound or hafnium compound and the aluminoxane obtained by mixing the components in advance may be fed to the reaction system, or the components may be separately fed to the reaction system. In either of the cases, the concentration and molar ratio of both the components in the reaction system have no particular limitation, but the concentration of the transition metals is preferably in the range of $10^{-3}$ to $10^{-10}$ mol/l, and the molar ratio of Al to M is preferably in the range of 100 or more, particularly 1,000 or more.

The olefin pressure in the reaction system has no particular limitation, but it is preferably in the range of the atmospheric pressure to 50 Kg/cm$^2$G. The polymerization temperature also has no particular limitation, but it is usually in the range of $-50°$ to $+230°$ C., preferably $-30°$ to $100°$ C. Adjustment of the molecular weight at the time of polymerization may be carried out e.g. by choice of temperature or introduction of hydrogen gas.

According to the present invention, a novel zirconium or hafnium compound having a bis-substituted-cyclopentadienyl ligand of a bridged structure is obtained. When the zirconium compound or hafnium compound is used as a catalyst component for oelfin polymerization, it is possible to obtain a stereoregular polymer with a good efficiency.

The present invention will be described in more detail by way of Examples.

EXAMPLE 1

Dimethylsilylbis(methylcyclopentadienyl)zirconium dichloride

In this Example, reactions were all carried out in an inert gas atmosphere. Further, the reaction solvent used was dried in advance. In a 200 ml capacity glass reaction vessel, dimethylbis(methylcyclopentadienyl)silane (3.5 g, 16 mmol) was dissolved in tetrahydrofuran (50 ml), followed by gradually dropwise adding a hexane solution (23 ml) of n-butyllithium (1.6 M)(M refers to mol/l) to the above solution under ice-cooling and agitating the mixture at room temperature for 2 hours to obtain a yellow transparent liquid ($Li_2[Me_2Si(MeC_5H_3)_2]$).

In a 500 ml capacity glass reaction vessel, zirconium tetrachloride (3.5 g, 15 mmol) was cooled down to $-78°$ C., followed by adding tetrahydrofuran (200 ml), thereafter gradually dropwise adding the yellow transparent liquid obtained above, at $-78°$ C., agitating the mixture at room temperature for 15 hours, distilling off the solvent from a yellow-orange color solution containing white precipitates, adding methylene chloride (200 ml) and then dilute hydrochloric acid (100 ml) under ice cooling, separating two layers, drying the methylene chloride layer over anhydrous sodium sulfate, distilling off methylene chloride, adding pentane, filtering off the resulting solids to obtain pale green solids (2.87 g), and recrystallizing the solids from hot heptane (400 ml) to obtain yellow-white crystals (2.02 g). The values of the physical properties of this compound are shown below. In addition, IR spectra were measured according to KBr method and $^1$H-NMR spectra were measured using CDCl$_3$ as solvent.

Elemental analysis value: ($C_{14}H_{18}Cl_2SiZr$); Calculated value (%): C: 44.66, H: 4.82; Observed value (%): C: 45.02, H: 4.91.

IR spectra: shown in FIG. 1.

NMR spectra: shown in FIG. 2.

EXAMPLE 2

Polymerization

Into a 1.5 l capacity SUS autoclave sufficiently purged with nitrogen gas were successively fed purified toluene (500 ml), methylaluminoxane made by Toyo Stauffer Chemical Co., Ltd. (molecular weight: 770) (4.0 mmol) and dimethylsilylbis(methylcyclopentadienyl)zirconium dichloride (0.005 mmol), followed by raising the temperature up to 30° C., continuously introducing propylene so as to keep the total pressure at 3 Kg/cm$^2$G to carry out polymerization for 2 hours, thereafter decomposing the catalyst component with methanol and drying the resulting polypropylene to obtain isotactic polypropylene (130 g). The catalyst activity was 142 Kg/g Zr.Hr and its molecular weight was 9,400.

EXAMPLE 3

Polymerization

Into a 1.5 l capacity SUS autoclave sufficiently purged with nitrogen gas were successively fed purified toluene (100 ml), methylaminoxane made by Toyo Stauffer Chemical Co., Ltd. (molecular weight: 770) (4.0 mmol) and dimethylsilylbis(methylcyclopentadienyl)zirconium dichloride (0.005 mmol), followed by raising the temperature up to 30° C., then continuously introducing propylene so as to keep the total pressure at 1 Kg/cm$^2$G, carrying out polymerization for 10 minutes, stopping the feed of propylene, purging propylene, adding purified hexane (1,000 ml), raising the temperature up to 30° C., continuously feeding propylene so as to keep the total pressure at 3 Kg/cm$^2$G, carrying out polymerization for 2 hours, thereafter decomposing the catalyst component with methanol, drying the resulting polypropylene to obtain isotactic polypropylene (125 g). The catalyst activity was 137 Kg/g Zr.hr.

COMPARATIVE EXAMPLE 1

Polymerization

Example 2 was repeated except that dimethylsilylbis(methylcyclopentadienyl)zirconium dichloride was replaced by dimethylsilylbis(cyclopentadienyl)zirconium dichloride to obtain atactic polypropylene (29 g). The catalyst activity was 32 Kg/g Zr.hr and its molecular weight was 5,300.

COMPARATIVE EXAMPLE 2

Polymerization

Example 2 was repeated except that dimethylsilylbis(methylcyclopentadienyl)zirconium dichloride was replaced by bis(methyl-t-butylcyclopentadienyl)zirconium dichloride to obtain atactic polypropylene (2.6 g). The catalyst activity was 2.9 Kg/g Zr.hr.

COMPARATIVE EXAMPLE 3

Polymerization

Into a 1.5 l capacity SUS autoclave sufficiently purged with nitrogen gas were successively added purified toluene (500 ml), methylaluminoxane made by Toyo Stauffer Chemical Co., Ltd. (molecular weight: 909) (6.3 mmol) and bis(methylcyclopentadienyl)zirconium dichloride (0.02 mmol), followed by raising the temperature up to 50° C., continuously introducing propylene into the mixture so as to keep the total pressure at 8 Kg/cm$^2$G, carrying out polymerization for 4 hours, decomposing the catalyst component with methanol after the reaction and drying the resulting polypropylene to obtain atactic polypropylene (220 g). The catalyst activity was 30 Kg/g Zr.hr.

EXAMPLE 4

Dimethylsilyl(cyclopentadienyl)(methylcyclopentadienyl)zirconium dichloride

All the reactions were carried out in an inert gas atmosphere. Further, the reaction solvent was dried in advance and used.

In a 200 ml capacity glass reaction vessel, dimethyl (cyclopentadienyl)(methylcyclopentadienyl)silane (3.4 g, 17 mmol) was dissolved in pentane (50 ml), followed by slowly dropwise adding a solution (24 ml) of n-butyllithium (1.6 M) under ice cooling, agitating the mixture at room temperature for 2 hours, distilling off the solvent to obtain white solids (Li$_2$[Me$_2$Si(C$_5$H$_4$)(Me-C$_5$H$_3$)]), and adding tetrahydrofuran (50 ml) thereto to obtain a yellow transparent liquid.

In a 500 ml capacity glass reaction vessel, zirconium tetrachloride (4.0 g, 17 mmol) was cooled down to −78° C., followed by adding tetrahydrofuran (200 ml), then slowly dropwise adding the yellow transparent liquid obtained above at −78° C., agitating the mixture at room temperature for one hour, heating it under reflux for one hour, allowing it to cool down, distilling off the solvent from a pale yellow solution containing white precipitates, adding methylene chloride (200 ml) and then dilute hydrochloric acid (100 ml) under ice cooling, separating the liquids, drying the methylene chloride layer over anhydrous sodium sulfate, distilling off methylene chloride, adding pentane, filtering off the resulting solids to obtain pale green solids (2.44 g) and recrystallizing them from hot heptane (400 ml) to obtain pale yellow crystals (1.18 g). The values of the physical properties of this compound are shown below. In addition, IR spectra were measured according to KBr method and $^1$HNMR spectra were measured using CDCl$_3$ as solvent.

Elemental analysis value: (C$_{13}$H$_{16}$Cl$_2$SiZr); Calculated value (%): C: 43.08, H: 4.45; Observed value (%): C: 42.86, H: 4.49.

IR spectra: shown in FIG. 3.

NMR spectra: shown in FIG. 4.

EXAMPLE 5

Polymerization

Into a 1.5 l capacity SUS autoclave sufficiently purged with nitrogen gas were successively added purified toluene (500 ml), methylaluminoxane made by Toyo Stauffer Chemical Co., Ltd. (molecular weight: 770) (4.0 mmol) and dimethylsilyl(cyclopentadienyl)-(methylcyclopentadienyl)zirconium dichloride (0.005 mmol), followed by raising the temperature up to 30° C., continuously introducing propylene so as to keep the total pressure at 3 Kg/cm$^2$G to carry out polymerization for 2 hours, decomposing the catalyst component with methanol after the reaction and drying the resulting polypropylene to obtain isotactic polypropylene (70 g). The catalyst activity was 77 Kg/g Zr.hr. Its molecular weight was 6,600.

EXAMPLE 6

Dimethylsilyl(cyclopentadienyl)(t-butylcyclopentadienyl)-zirconium dichloride All the reactions were carried out in an inert gas atmosphere. Further, the reaction solvent was dried in advance and used. In a 200 ml capacity glass reaction vessel, dimethyl(cyclopentadienyl)(t-butylcyclopentadienyl)silane (5.1 g, 21 mmol) was dissolved in pentane (50 ml), followed by slowly dropwise adding a hexane solution (29 ml) of n-butyllithium (1.6 M) under ice cooling, agitating the mixture at room temperature for 2 hours, distilling off the solvent to obtain white solids (Li$_2$[Me$_2$Si(C$_5$H$_4$)(t-Bu-C$_5$H$_3$)]) and adding thereto tetrahydrofuran (50 ml) to obtain a yellow transparent liquid.

In a 500 ml glass reaction vessel, zirconium tetrachloride (5.0 g, 21 mmol) was cooled down to −78° C., followed by adding tetrahydrofuran (200 ml), slowly dropwise adding the yellow transparent liquid obtained above at −78° C., agitating the mixture at room temperature for 2 hours, heating it under reflux for 2 hours, allowing it to cool down, distilling off the solvent from the resulting pale yellow solution containing white precipitates, adding methylene chloride (200 ml) and then dilute hydrochloric acid (100 ml) under ice cooling, separating the liquids, drying the methylene chloride layer over anhydrous sodium sulfate, distilling off methylene chloride, adding pentane, filtering off the resulting solids to obtain pale green solids and recrystallizing them from hot heptane (400 ml) to obtain pale yellow crystals (0.8 g). The values of the physical properties of the compound are shown below. In addition, its IR spectra were measured according to KBr method and $^1$H-NMR spectra were measured using CDCl$_3$ as solvent.

Elemental analysis value: (C$_{16}$H$_{22}$Cl$_2$SiZr); Calculated value (%): C: 47.50, H: 5.48; Observed value (%): C: 47.65, H: 5.61.

IR spectra: shown in FIG. 5.
NMR spectra: shown in FIG. 6.

EXAMPLE 7

Polymerization

Into a 1.5 l capacity SUS autoclave sufficiently purged with nitrogen gas were successively added purified toluene (500 ml), methylaluminoxane made by Toyo Stauffer Chemical Co., Ltd. (molecular weight: 770) (4.0 mmol) and dimethylsilyl(cyclopentadienyl)(t-butylcyclopentadienyl)zirconium dichloride (0.005 mmol), followed by raising the temperature up to 30° C., continuously introducing propylene so as to keep the total pressure at 3 Kg/cm$^2$G, carrying out polymerization for 2 hours, decomposing the catalyst component with methanol after the reaction and drying the resulting polypropylene to obtain isotactic polypropylene (75 g). The catalyst activity was 82 Kg/g Zr.hr. Further, its molecular weight was 4,300.

EXAMPLE 8

Dimethylsilyl(methylcyclopentadienyl)(t-butylcyclopentadienyl)zirconium dichloride All the reactions were carried out in an inert gas atmosphere. Further, the reaction solvent was dried in advance and used. In a 200 ml capacity glass reaction vessel, dimethyl(methylcyclopentadienyl)(t-butylcyclopentadienyl)silane (3.9 g, 15 mmol) was dissolved in pentane (50 ml), followed by slowly dropwise adding a hexane solution (20 ml) of n-butyllithium (1.6 M) under ice cooling, agitating the mixture at room temperature for 2 hours, distilling off the solvent to obtain white solids (Li$_2$[Me$_2$Si(Me-C$_5$H$_3$)(t-Bu-C$_5$H$_3$)]) and adding thereto tetrahydrofuran (50 ml) to obtain a yellow transparent liquid.

In a 500 ml capacity glass reaction vessel, zirconium tetrachloride (3.5 g, 15 mmol) was cooled down to −78° C., followed by adding tetrahydrofuran (200 ml), slowly dropwise adding the yellow transparent liquid obtained above at −78° C., agitating the mixture at room temperature for 18 hours, heating it under reflux for 4 hours, allowing it to cooling down, distilling off the solvent from a pale yellow solution containing white precipitates, adding methylene chloride (200 ml) and then dilute hydrochloric acid (100 ml), separating the liquids, drying the methylene chloride layer over anhydrous sodium sulfate, distilling off methylene chloride, adding pentane and filtering to obtain pale yellow crystals (0.37 g) from the pale yellow filtrate. The values of the physical properties of this compound are shown below. In addition, the IR spectra were measured according to KBr method and the $^1$H-NMR spectra were measured using CDCl$_3$ as solvent.

Elemental analysis values: (C$_{17}$H$_{24}$Cl$_2$SiZr); Calculated value (%): C: 48.78, H: 5.78; Observed value (%): C: 48.81, H: 5.82.

IR spectra: shown in FIG. 7.
NMR spectra: shown in FIG. 8.

EXAMPLE 9

Polymerization

Into a 1.5 l capacity SUS autoclave sufficiently purged with nitrogen gas were successively added purified toluene (500 ml), methylaluminoxane made by Toyo Stauffer Chemical Co., Ltd. (molecular weight: 770) (4.0 mmol) and dimethylsilyl(methylcyclopentadienyl)(t-butylcyclopentadienyl)zirconium dichloride (0.005 mmol), followed by raising the temperature up to 30° C., continuously introducing propylene so as to keep the total pressure at 3 Kg/cm$^2$G, carrying out polymerization for 2 hours, decomposing the catalyst component with methanol after the reaction and drying the resulting polypropylene to obtain isotactic polypropylene (59 g). The catalyst activity was 65 Kg/g Zr.hr. Further, its molecular weight was 6,400.

EXAMPLE 10

Dimethylsilylbis(t-butylcyclopentadienyl)zirconium dichloride

All the reactions were carried out in an inert gas atmosphere. Further, the reaction solvent was dried in advance and used. In a 200 ml capacity glass reaction vessel, dimethylbis(t-butylcyclopentadienyl)silane (4.6 g, 15 mmol) was dissolved in pentane (50 ml), followed by slowly dropwise adding a hexane solution (21 ml) of n-butyllithium (1.6 M) under ice cooling, agitating the mixture at room temperature for 4 hours, distilling off the solvent to obtain white solids (Li$_2$[Me$_2$Si(t-Bu-C$_5$H$_3$)$_2$]) and adding tetrahydrofuran (50 ml) to obtain a yellow transparent liquid.

In a 500 ml capacity glass reaction vessel, zirconium tetrachloride (3.5 g, 15 mmol) was cooled down to −78° C., followed by adding tetrahydrofuran (250 ml), slowly dropwise adding the yellow transparent liquid obtained above at −78° C., allowing the mixture to stand, returning the temperature to room temperature, heating it under reflux for 84 hours, allowing the resulting material to cool down, distilling off the solvent from a yellow transparent solution, adding methylene chloride (300 ml) and then dilute hydrochloric acid (100 ml) under ice cooling, separating the liquids, drying the methylene chloride layer over anhydrous sodium sulfate, distilling off methylene chloride, adding pentane and filtering to obtain yellow-white crystals (2.35 g) from a yellow filtrate. The values of the physical properties of this compound are shown below. In addition, the IR spectra were measured according to KBr method and the $^1$H-NMR spectra were measured using CDCl$_3$ as solvent.

Elemental analysis values: (C$_{20}$H$_{30}$Cl$_2$SiZr); Calculated value (%): C: 52.15, H: 6.56; Observed value (%): C: 52.01, H: 6.58.

IR spectra: shown in FIG. 9.
NMR spectra: shown in FIG. 10.

EXAMPLE 11

Polymerization

Into a 1.5 l capacity SUS autoclave sufficiently purged with nitrogen gas were successively added purified toluene (500 ml), methylaluminoxane made by Toyo Stauffer Chemical Co., Ltd. (molecular weight: 770) (4.0 mmol) and dimethylsilylbis(t-butylcyclopentadienyl)zirconium dichloride (0.005 mmol), followed by raising the temperature up to 30° C., continuously introducing propylene so as to keep the total pressure at 3 Kg/cm$^2$G, carrying out polymerization for 2 hours, decomposing the catalyst component with methanol after the reaction and drying the resulting polypropylene to obtain isotactic polypropylene (3.1 g). The catalyst activity was 3.4 Kg/g Zr.hr. Its molecular weight was 9,600.

EXAMPLE 12

Dimethylgermylbis(methylcyclopentadienyl)zirconium dichloride

All the reactions were carried out in an inert gas atmosphere. Further, the reaction solvent was dried in advance and used. In a 200 ml capacity glass reaction vessel, dimethylbis(methylcyclopentadienyl)germane (1.2 g, 8 mmol) was dissolved in pentane (50 ml), followed by slowly dropwise adding a hexane solution (11 ml) of n-butyllithium (1.6 M) under ice cooling, agitating the mixture at room temperature for 2 hours, distilling off the solvent to obtain white solids (Li$_2$[Me$_2$Ge(Me-C$_5$H$_3$)$_2$]), adding thereto tetrahydrofuran (50 ml) to obtain a yellow transparent liquid.

In a 500 ml capacity glass reaction vessel, zirconium tetrachloride (1.8 g, 8 mmol) was cooled down to −78° C., followed by adding tetrahydrofuran (150 ml), slowly dropwise adding the yellow transparent liquid obtained above at −78° C., agitating the mixture at room temperature for 14 hours, heating it under reflux for 2 hours, allowing the resulting material to cool down, distilling off the solvent from a yellow transparent solution, adding methylene chloride (200 ml) and then dilute hydrochloric acid (100 ml) under ice cooling, separating the liquids, drying the methylene chloride layer over anhydrous sodium sulfate, distilling off methylene chloride, adding pentane, filtering and concentrating to obtain yellow-white crystals (0.31 g) from a pale yellow filtrate. The values of the physical properties of this compound are shown below. In addition, the IR spectra were measured according to KBr method and $^1$H-NMR spectra were measured using CDCl$_3$ as solvent.

Elemental analysis values: (C$_{14}$H$_{18}$Cl$_2$GeZr); Calculated value (%): C: 39.94, H: 4.31; Observed value (%): C: 40.38, H: 4.38.

IR spectra: shown in FIG. 11.
NMR spectra: shown in FIG. 12.

EXAMPLE 13

Polymerization

Into a 1.5 l capacity SUS autoclave sufficiently purged with nitrogen gas, purified toluene (500 ml), methylaluminoxane made by Toyo Stauffer Chemical Co., Ltd. (molecular weight: 770) (4.0 mmol) and dimethylgermylbis(methylcyclopentadienyl)zirconium dichloride (0.005 mmol) were successively added, followed by raising the temperature up to 30° C., continuously introducing propylene so as to keep the total pressure at 3 Kg/cm$^2$G, carrying out polymerization for 2 hours, decomposing the catalyst component with methanol after the reaction and drying the resulting polypropylene to obtain isotactic polypropylene (2 5 g). The catalyst activity was 27 Kg/g Zr.hr. Its molecular weight was 7,600.

EXAMPLE 14

Cyclotetramethylenesilyl(cyclopentadienyl)(methylcyclopentadienyl)zirconium dichloride All the reactions were carried out in an inert gas atmosphere. Further, the reaction solvent was dried in advance and used. In a 200 ml capacity glass reaction vessel, cyclotetramethylene(cyclopentadienyl)(methylcyclopentadienyl)silane (3.4 g, 15 mmol) was dissolved in pentane (50 ml), followed by slowly dropwise adding a hexane solution (22 ml) of n-butyllithium (1.6 M), agitating the mixture at room temperature for 3 hours, distilling off the solvent to obtain white solids (Li$_2$[(CH$_2$)$_4$Si(C$_5$H$_4$)(MeC$_5$H$_3$)]), and adding thereto tetrahydrofuran (50 ml) to obtain a yellow transparent liquid.

In a 500 ml capacity glass reaction vessel, zirconium tetrachloride (3.5 g, 15 mmol) was cooled down to −78° C., adding tetrahydrofuran (250 ml), slowly dropwise adding the yellow transparent liquid obtained above at −78° C., agitating the mixture at room temperature for 48 hours, distilling off the solvent from a yellow solution containing white precipitates, adding methylene chloride (200 ml), filtering off the resulting white solids, concentrating the resulting yellow filtrate, adding pentane and cooling the mixture down to −30° C. to obtain yellow-white crystals (0.39 g). The values of the physical properties of this compound are shown below. In addition, its IR spectra were measured according to KBr method and its $^1$H-NMR spectra were measured using CDCl$_3$ as solvent.

Elemental analysis values: (C$_{15}$H$_{18}$Cl$_2$SiZr); Calculated value (%): C: 46.37, H: 4.67; Observed value (%): C: 47.03, H: 4.82.

IR spectra: shown in FIG. 13.
NMR spectra: shown in FIG. 14.

EXAMPLE 15

Polymerization

Into a 1.5 l capacity SUS autoclave sufficiently purged with nitrogen gas, purified toluene (500 ml), methylaluminoxane made by Toyo Stauffer Chemical Co., Ltd. (molecular weight: 770) (4.0 mmol) and cyclotetramethylenesilyl(cyclopentadienyl)(methylcyclopentadienyl)zirconium dichloride (0.005 mmol) were successively added, followed by raising the temperature up to 30° C., continuously introducing propylene so as to keep the total pressure at 3 Kg/cm$^2$G, carrying out polymerization for 2 hours, decomposing the catalyst component with methanol after the reaction and drying the resulting polypropylene to obtain isotactic polypropylene (3.6 g). The catalyst activity was 3.9 Kg/g Zr.hr. Its molecular weight was 4,200.

EXAMPLE 16

Dimethylsilyl(methylcyclopentadienyl)(dimethylcyclopentadienyl)zirconium dichloride All the reactions were carried out in an inert gas atmosphere. Further, the reaction solvent was dried in advance and used. In a 200 ml glass reaction vessel, dimethyl(methylcyclopentadienyl)(dimethylcyclopentadienyl)silane (3.5 g, 15 mmol) was dissolved in pentane (50 ml), followed by slowly dropwise adding a hexane solution (22 ml) of n-butyllithium (1.6 M) under ice cooling, agitating the mixture at room temperature for 5 hours, distilling off the solvent to obtain white solids ($Li_2[Me_2Si(Me-C_5H_3)(Me_2-C_5H_2)]$), and adding thereto tetrahydrofuran (50 ml) to obtain a yellow-brown transparent liquid.

In a 500 ml glass reaction vessel, zirconium tetrachloride (3.5 g, 15 mmol) was cooled down to $-78°$ C., followed by adding tetrahydrofuran (250 ml), slowly dropwise adding the yellow-brown transparent liquid obtained above at $-78°$ C., agitating the mixture at room temperature for 18 hours, heating it under reflux for 6 hours, distilling off the solvent from the resulting yellow solution, adding methylene chloride (300 ml), filtering off the resulting white solids, concentrating the resulting yellow filtrate, adding pentane, filtering the resulting solids and recrystallizing the solids from hot heptane (200 ml) to obtain yellow-white crystals (1.08 g). The values of the physical properties of this compound are shown below. In addition, its IR spectra were measured according to KBr method and its $^1$-NMR spectra were measured using $CDCl_3$ as solvent.

Elemental analysis values: ($C_{15}H_{20}Cl_2SiZr$); Calculated value: C: 46.13, H: 5.16; Observed value: C: 46.22, H: 5.16.

IR spectra: shown in FIG. 15.
NMR spectra: shown in FIG. 16.

EXAMPLE 17

Polymerization

Into a 1.5 l capacity SUS autoclave sufficiently purged with nitrogen gas, purified toluene (500 ml), methylaluminoxane made by Toyo Stauffer Chemical Co., Ltd. (molecular weight: 770) (4.0 mmol) and dimethylsilyl(methycyclopentadienyl) (dimethylcyclopentadienyl)zirconium dichloride (0.005 mmol) were successively added, followed by raising the temperature up to 30° C., continuously introducing propylene so as to keep the total pressure at 3 Kg/cm$^2$G, carrying out polymerization for 2 hours, decomposing the catalyst component with methanol and drying the resulting polypropylene to obtain isotactic polypropylene (45 g). The catalyst activity was 49 Kg/g Zr.hr. Its molecular weight was 5,600.

EXAMPLE 18

Dimethylsilylbis(methylcyclopentadienyl)hafnium dichloride

All the reactions were carried out in an inert gas atmosphere. Further, the reaction solvent was dried in advance and used. In a 200 ml glass reaction vessel, dimethylbis(methylcyclopentadienyl)silane (3.3 g, 15 mmol) was dissolved in tetrahydrofuran (50 ml), followed by slowly dropwise adding a hexane solution (21 ml) of n-butyllithium (1.6 M) under ice cooling and agitating the mixture at room temperature for 2 hours to obtain a yellow transparent liquid ($Li_2[Me_2Si(-MeC_5H_3)_2]$).

In a 500 ml capacity glass reaction vessel, hafnium tetrachloride (4.8 g, 15 mmol) was cooled down to $-78°$ C., followed by adding tetrahydrofuran (200 ml), slowly dropwise adding the yellow transparent liquid obtained above at $-78°$ C., agitating the mixture at room temperature for 17.5 hours, heating it under reflux for one hour, allowing the resulting material to cool down, distilling off the solvent from a yellow-orange color solution containing white precipitates, adding methylene chloride (200 ml) and then dilute hydrochloric acid (100 ml), separating the liquids, drying the methylene chloride layer over anhydrous sodium sulfate, distilling off methylene chloride, adding pentane, filtering off insoluble solids, cooling a yellow filtrate to obtain yellow-white crystals (2.02 g). The values of the physical properties of this compound are shown below. In addition, its IR spectra were measured according to KBr method and its $^1$H-NMR spectra were measured using $CDCl_3$ as solvent.

IR spectra: shown in FIG. 17.
NMR spectra: shown in FIG. 18.

EXAMPLE 19

Polymerization

Into a 1.5 l capacity SUS autoclave sufficiently purged with nitrogen gas, purified toluene (500 ml), methylaluminoxane made by Toyo Stauffer Chemical Co., Ltd. (molecular weight: 770) (4.0 mmol) and dimethylsilylbis(methylcyclopentadienyl)hafnium dichloride (0.005 mmol) were successively added, followed by raising the temperature up to 30° C., continuously introducing propylene so as to keep the total pressure at 3 Kg/cm$^2$G, carrying out polymerization for 2 hours, decomposing the catalyst component with methanol after the reaction and drying the resulting polypropylene to obtain isotactic polypropylene (16 g). The catalyst activity was 8.9 Kg/g Hf.hr, and its molecular weight was 66,800.

EXAMPLE 20

Dimethylsilyl(cyclopentadienyl)(methylcyclopentadienyl)-hafnium dichloride

All the reactions were carried out in an inert gas atmosphere. Further, the reaction solvent was dried in advance and used. In a 200 ml glass reaction vessel, dimethyl(cyclopentadienyl)(methylcyclopentadienyl)-silane (3.0 g, 15 mmol) was dissolved in pentane (50 ml), followed by slowly dropwise adding a hexane solution (20 ml) of n-butyllithium (1.6M) under ice cooling, agitating the mixture at room temperature for 2 hours and distilling off the solvent to obtain white solids ($Li_2[Me_2Si(C_5H_4)(Me-C_5H_3)]$), and adding thereto tetrahydrofuran (50 ml) to obtain a yellow transparent liquid.

In a 500 ml capacity glass reaction vessel, hafnium tetrachloride (4.8 g, 15 mmol) was cooled down to $-78°$ C., followed by adding tetrahydrofuran (200 ml), slowly dropwise adding the yellow transparent liquid obtained above at $-78°$, agitating the mixture at room temperature for 14 hours, distilling off the solvent from a yellow solution containing white solids, adding methylene chloride (200 ml) and then dilute hydrochloric acid (100 ml) under ice cooling, separating the liquids, drying methylene chloride layer over anhydrous sodium sulfate, distilling off methylene chloride, adding pentane, filtering off the resulting solids to obtain pale green solids (2.22 g) and recrystallizing the crystals from hot heptane (200 ml) to obtain pale yellow-white crystals (0.94 g). The values of the physical properties of this compound are shown below. In addition, its IR spectra were measured according to KBr method and its $^1$H-NMR spectra were measured using CDCl$_3$ as solvent.

IR spectra: shown in FIG. 19.
NMR spectra: shown in FIG. 29.

EXAMPLE 21
Polymerization

Into a 1.5 l capacity SUS autoclave sufficiently purged with nitrogen gas, purified toluene (500 ml), methylaluminoxane made by Toyo Stauffer Chemical Co., Ltd. (molecular weight: 770) (4.0 mmol) and diemethylsilyl(cyclopentadienyl)(methylcyclopentadienyl)hafnium dichloride (0.005 mmol) were successively added, followed by raising the temperature up to 30° C., continuously introducing propylene so as to keep the total pressure at 3 Kg/cm$^2$G, carrying out polymerization for 2 hours, decomposing the catalyst component with methanol and drying the resulting polypropylene to obtain isotactic polypropylene (0.6 g). The catalyst activity was 0.34 Kg/g Hf.hr. and its molecular weight was 52,800.

EXAMPLE 22
Dimethylsilylbis(t-butylcyclopentadienyl)hafnium dichloride

All the reactions were carried out in an inert gas atmosphere. Further, the reaction solvent was dried in advance and used. In a 200 ml capacity glass reaction vessel, dimethylbis(t-butylcyclopentadienyl)silane (4.8 g, 16 mmol) was dissolved in pentane (50 ml), followed by slowly dropwise adding a hexane solution (22 ml) of n-butyllithium (1.6 M) under ice cooling, agitating the mixture at room temperature for 4 hours, distilling off the solvent to obtain white solids (Li$_2$[Me$_2$Si(t-Bu-C$_5$H$_3$)$_2$], and adding thereto tetrahydrofuran (60 ml) to obtain a yellow transparent liquid.

In a 500 ml capacity glass reaction vessel, hafnium tetrachloride (5.1 g, 16 mmol) was cooled down to −78° C., followed by adding tetrahydrofuran (250 ml), slowly dropwise adding the yellow transparent liquid at −78° C., allowing the mixture to stand to return the temperature to room temperature, heating it under reflux for 84 hours, allowing the resulting material to cool down, distilling off the solvent from a yellow-orange color transparent solution, adding methylene chloride (300 ml) and then dilute hydrochloric acid (100 ml) under ice cooling, separating the liquids, drying the methylene chloride layer over anhydrous sodium sulfate, distilling off methylene chloride, adding pentane, filtering, concentrating the resulting yellow filtrate and cooling to obtain pale yellow crystals (1.41 g). The values of the physical properties of this compound are shown below. In addition, its IR spectra were measured according to KBr method and its $^1$H-NMR spectra were measured using CDCl$_3$ as solvent.

Elemental analysis values: (C$_{20}$H$_{30}$Cl$_2$SiHf); Calculated value (%): C: 43.84, H: 5.52; Observed value (%): C: 44.05, H: 5.62.

IR spectra: shown in FIG. 21.
NMR spectra: shown in FIG. 22.

EXAMPLE 23
Polymerization

Into a 1.5 l capacity SUS autoclave sufficiently purged with nitrogen gas, purified toluene (500 ml), methylaluminoxane made by Toyo Stauffer Chemical Co., Ltd. (molecular weight: 770) (4.0 mmol) and dimethylsilylbis(t-butylcyclopentadienyl)hafnium dichloride (0.005 mmol) were successively added, followed by raising the temperature up to 30° C., continuously introducing propylene so as to keep the total pressure at 3 Kg/cm$^2$G, carrying out polymerization for 2 hours, decomposing the catalyst component with methanol after the reaction and drying the resulting polypropylene to obtain isotactic polypropylene (0.3 g). The catalyst activity was 0.17 Kg/g Hf.hr. Further, its molecular weight was 17,200.

COMPARATIVE EXAMPLE 4
Polymerization

Into a 1.5 l capacity SUS autoclave sufficiently purged with nitrogen gas, purified toluene (500 ml), methylaluminoxane made by Toyo Stauffer Chemical Co., Ltd. (molecular weight: 770) (4.0 mmol) and dimethylsilylbis(cyclopentadienyl)hafnium dichloride (0.005 mmol) were successively added, followed by raising the reaction up to 30° C., continuously introducing propylene so as to keep the total pressure at 3 Kg/cm$^2$G, carrying out polymerization for 2 hours, decomposing the catalyst component with methanol after the reaction and drying the resulting polypropylene to obtain atactic polypropylene (3.5 g). The catalyst activity was 2.0 Kg/g Hf.hr.

What we claim is:

1. A transition-metal compound expressed by the formula (I)

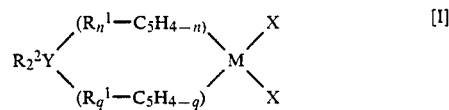

wherein M represents zirconium or hafnium; Y represents silicon or germanium; R$^1_n$-C$_5$H$_{4-n}$ and R$^1_q$-C$_5$H$_{4-q}$ each represent an unsubstituted or substituted cyclopentadienyl group; n and q each represent an integer of 0 to 4, but cases of n=q=0 and n=q=4 are excluded; the respective R$^1$s may be the same or different and each represent silyl group or a hydrocarbon radical; the respective R$^2$s may be the same or different and each represent hydrogen atom or a hydrocarbon radical; and the respective Xs may be the same or different and each represent hydrogen atom, a halogen atom or a hydrocarbon radical.

2. A catalyst for producing a stereoregular olefin polymer, which catalyst comprises as its effective components, (A) a transition-metal compound expressed by the formula

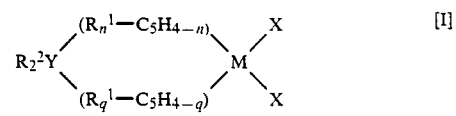

wherein M represents a transition-metal compound of zirconium or hafnium; Y represents silicon or germanium; $R^1{}_n\text{-}C_5H_{4-n}$ and $R^1{}_q\text{-}C_5H_{4-q}$ each represent an unsubstituted or substituted cyclopentadienyl group; n and q each represent an integer of 0 to 4, but cases of n=q=0 and n=q=4 are excluded; the respective $R^1$s may be same or different and each represent a silyl group or a hydrocarbon radical, but the site of $R^1$ on the cyclopentadienyl ring and the kind of $R^1$ has a configuration wherein any symmetry plane containing M is absent; the respective $R^2$s may be the same or different and each represent hydrogen atom or a hydrocarbon radical; and the respective Xs may be the same or different and each represent hydrogen atom, a halogen atom or a hydrocarbon radical, and (B) an aluminoxane expressed by the formula [II] or the formula [III]

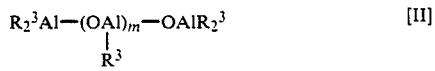

[II]

[III]

wherein m represents an integer of 4 to 30 and $R^3$ represents a hydrocarbon radical.

* * * * *